United States Patent
Belson

(10) Patent No.: US 10,328,239 B2
(45) Date of Patent: *Jun. 25, 2019

(54) INTRAVENOUS CATHETER AND INSERTION DEVICE WITH REDUCED BLOOD SPATTER

(71) Applicant: Vascular Pathways, Inc., Salt Lake City, UT (US)

(72) Inventor: Amir Belson, Los Altos, CA (US)

(73) Assignee: Vascular Pathways, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/481,773

(22) Filed: Apr. 7, 2017

(65) Prior Publication Data

US 2017/0209668 A1 Jul. 27, 2017

Related U.S. Application Data

(63) Continuation of application No. 14/192,541, filed on Feb. 27, 2014, now Pat. No. 9,616,201, which is a
(Continued)

(51) Int. Cl.
*A61M 25/01* (2006.01)
*A61M 25/09* (2006.01)
(Continued)

(52) U.S. Cl.
CPC ............ *A61M 25/01* (2013.01); *A61M 5/158* (2013.01); *A61M 25/00* (2013.01);
(Continued)

(58) Field of Classification Search
CPC .......... A61M 25/0606; A61M 25/0097; A61M 25/0631; A61M 25/09041;
(Continued)

(56) References Cited

U.S. PATENT DOCUMENTS 2,211,975 A 8/1940 Hendrickson
2,259,488 A 10/1941 Raiche
(Continued)

FOREIGN PATENT DOCUMENTS

AU 691141 B2 5/1998
AU 710967 B2 9/1999
(Continued)

OTHER PUBLICATIONS

Access Scientific, The PICC Wand® Product Data Sheet, Revision F, May 22, 2012.
(Continued)

*Primary Examiner* — Jenna Zhang
(74) *Attorney, Agent, or Firm* — Rutan & Tucker, LLP

(57) ABSTRACT

A catheter insertion device and method for insertion. The catheter insertion device can include a housing, a needle attached to a needle carrier, a catheter including a catheter shaft attached to a catheter hub, and a guidewire. The guidewire can include a coil tip positioned in a lumen of the needle. The method for insertion can include inserting a distal end of the needle and the catheter shaft into a blood vessel of a patient, advancing the coil tip out of the needle lumen and into the blood vessel, advancing the catheter over the guidewire, and withdrawing the guidewire and the needle from the catheter. The coil tip can include a straightened configuration and a coiled configuration. The coil tip can transition from the straightened configuration in the needle lumen to the coiled configuration in the blood vessel.

13 Claims, 10 Drawing Sheets

Related U.S. Application Data continuation of application No. 13/358,099, filed on Jan. 25, 2012, now Pat. No. 8,690,833.

(60) Provisional application No. 61/438,197, filed on Jan. 31, 2011.

(51) Int. Cl.
*A61M 25/06* (2006.01)
*A61M 5/158* (2006.01)
*A61M 25/00* (2006.01)

(52) U.S. Cl.
CPC ........ *A61M 25/0097* (2013.01); *A61M 25/06* (2013.01); *A61M 25/065* (2013.01); *A61M 25/0606* (2013.01); *A61M 25/0631* (2013.01); *A61M 25/09* (2013.01); *A61M 25/0905* (2013.01); *A61M 25/09041* (2013.01); *A61M 25/0637* (2013.01); *A61M 2005/1583* (2013.01); *A61M 2025/09066* (2013.01); *A61M 2025/09175* (2013.01)

(58) Field of Classification Search
CPC .............. A61M 25/0637; A61M 5/158; A61M 2025/09175; A61M 2005/1583; A61M 25/00; A61M 25/0905; A61M 25/09; A61M 25/065; A61M 25/06; A61M 25/01; A61M 2025/09066
See application file for complete search history.

(56) References Cited

U.S. PATENT DOCUMENTS

| | | |
|---|---|---|
| 2,330,400 A | 9/1943 | Winder |
| D138,589 S | 8/1944 | Brandenburg |
| 3,185,151 A | 5/1965 | Czorny |
| 3,297,030 A | 1/1967 | Czorny et al. |
| 3,416,567 A | 12/1968 | von Dardel et al. |
| 3,469,579 A | 9/1969 | Hubert |
| 3,500,828 A | 3/1970 | Podhora |
| 3,552,384 A | 1/1971 | Pierie et al. |
| 3,572,334 A | 3/1971 | Petterson |
| 3,585,996 A * | 6/1971 | Reynolds ........... A61M 25/0111 604/158 |
| 3,589,361 A | 6/1971 | Loper et al. |
| 3,592,192 A | 7/1971 | Harautuneian |
| 3,595,230 A | 7/1971 | Suyeoka et al. |
| 3,610,240 A | 10/1971 | Harautuneian |
| 3,682,173 A | 8/1972 | Center |
| 3,884,242 A | 5/1975 | Bazell et al. |
| 3,921,631 A | 11/1975 | Thompson |
| 3,995,628 A | 12/1976 | Gula et al. |
| 4,027,668 A | 6/1977 | Dunn |
| 4,037,600 A | 7/1977 | Poncy et al. |
| 4,079,738 A | 3/1978 | Dunn et al. |
| 4,106,506 A | 8/1978 | Koehn et al. |
| 4,177,809 A | 12/1979 | Moorehead |
| 4,292,970 A | 10/1981 | Hession, Jr. |
| 4,317,445 A | 3/1982 | Robinson |
| 4,345,602 A | 8/1982 | Yoshimura et al. |
| 4,354,491 A | 10/1982 | Marbry |
| 4,368,730 A | 1/1983 | Sharrock |
| 4,387,879 A | 6/1983 | Tauschinski |
| 4,417,886 A | 11/1983 | Frankhouser et al. |
| 4,449,693 A | 5/1984 | Gereg |
| 4,456,017 A | 6/1984 | Miles |
| 4,464,171 A | 8/1984 | Garwin |
| 4,509,534 A | 4/1985 | Tassin, Jr. |
| 4,509,945 A | 4/1985 | Kramann et al. |
| 4,511,359 A | 4/1985 | Vaillancourt |
| 4,512,766 A | 4/1985 | Vailancourt |
| 4,581,019 A | 4/1986 | Curelaru et al. |
| 4,585,440 A | 4/1986 | Tchervenkov et al. |
| D287,877 S | 1/1987 | Holewinski et al. |
| 4,728,322 A | 3/1988 | Walker et al. |
| 4,738,659 A | 4/1988 | Sleiman |
| 4,747,831 A | 5/1988 | Kulli |
| 4,767,407 A | 8/1988 | Foran |
| 4,772,264 A | 9/1988 | Cragg |
| 4,772,267 A | 9/1988 | Brown |
| 4,781,703 A | 11/1988 | Walker et al. |
| 4,792,531 A | 12/1988 | Kakihana |
| 4,798,193 A | 1/1989 | Giesy et al. |
| 4,813,934 A | 3/1989 | Engelson et al. |
| 4,826,070 A | 5/1989 | Kakihana |
| 4,828,547 A | 5/1989 | Sahi et al. |
| 4,834,708 A | 5/1989 | Pillari |
| 4,834,718 A | 5/1989 | McDonald |
| 4,840,613 A | 6/1989 | Balbierz |
| 4,840,622 A | 6/1989 | Hardy |
| 4,842,591 A | 6/1989 | Luther |
| 4,846,812 A | 7/1989 | Walker et al. |
| 4,869,259 A | 9/1989 | Elkins |
| D304,079 S | 10/1989 | McFarlane |
| 4,871,358 A | 10/1989 | Gold |
| 4,874,377 A | 10/1989 | Newgard et al. |
| 4,883,461 A | 11/1989 | Sawyer |
| 4,883,699 A | 11/1989 | Aniuk et al. |
| 4,894,052 A | 1/1990 | Crawford |
| 4,895,346 A | 1/1990 | Steigerwald |
| 4,900,307 A | 2/1990 | Kulli |
| 4,906,956 A | 3/1990 | Kakihana |
| 4,908,021 A | 3/1990 | McFarlane |
| 4,909,793 A | 3/1990 | Vining et al. |
| 4,911,691 A | 3/1990 | Aniuk et al. |
| 4,913,704 A | 4/1990 | Kurimoto |
| 4,917,102 A | 4/1990 | Miller et al. |
| 4,917,668 A | 4/1990 | Haindl et al. |
| 4,917,671 A | 4/1990 | Chang |
| 4,929,235 A | 5/1990 | Merry et al. |
| 4,935,010 A | 6/1990 | Cox et al. |
| 4,944,725 A | 7/1990 | McDonald |
| 4,944,728 A | 7/1990 | Carrell et al. |
| 4,955,863 A | 9/1990 | Walker et al. |
| 4,961,729 A | 10/1990 | Vaillancourt |
| 4,966,586 A | 10/1990 | Vaillancourt |
| 4,966,589 A | 10/1990 | Kaufman |
| 4,994,042 A | 2/1991 | Vadher |
| 4,994,047 A | 2/1991 | Walker et al. |
| 4,995,866 A | 2/1991 | Amplatz et al. |
| 5,007,901 A | 4/1991 | Shields |
| 5,009,642 A | 4/1991 | Sahi |
| 5,019,048 A | 5/1991 | Margolin |
| 5,019,049 A | 5/1991 | Haining |
| D318,733 S | 7/1991 | Wyzgala |
| 5,034,347 A | 7/1991 | Kakihana |
| 5,047,013 A | 9/1991 | Rossdeutscher |
| D321,250 S | 10/1991 | Jepson et al. |
| 5,053,014 A | 10/1991 | Van Heugten |
| 5,054,501 A | 10/1991 | Chuttani et al. |
| 5,061,254 A | 10/1991 | Karakelle et al. |
| 5,064,416 A | 11/1991 | Newgard et al. |
| 5,078,694 A | 1/1992 | Wallace |
| 5,078,696 A | 1/1992 | Nedbaluk |
| 5,078,702 A | 1/1992 | Pomeranz |
| 5,084,023 A | 1/1992 | Lemieux |
| 5,085,645 A | 2/1992 | Purdy et al. |
| 5,088,984 A | 2/1992 | Fields |
| 5,093,692 A | 3/1992 | Su et al. |
| 5,098,392 A | 3/1992 | Fleischhacker et al. |
| 5,098,395 A | 3/1992 | Fields |
| 5,098,396 A | 3/1992 | Taylor et al. |
| 5,098,405 A | 3/1992 | Peterson et al. |
| 5,108,375 A | 4/1992 | Harrison et al. |
| 5,108,376 A | 4/1992 | Bonaldo |
| 5,112,312 A | 5/1992 | Luther |
| 5,116,323 A | 5/1992 | Kreuzer et al. |
| 5,120,317 A | 6/1992 | Luther |
| 5,125,906 A | 6/1992 | Fleck |
| 5,135,487 A | 8/1992 | Morrill et al. |
| 5,137,515 A | 8/1992 | Hogan |
| 5,149,326 A | 9/1992 | Woodgrift et al. |
| 5,154,703 A | 10/1992 | Bonaldo |

(56) References Cited

U.S. PATENT DOCUMENTS

| | | |
|---|---|---|
| 5,156,590 A | 10/1992 | Vilmar |
| 5,156,596 A | 10/1992 | Balbierz et al. |
| 5,158,544 A | 10/1992 | Weinstein |
| 5,167,637 A | 12/1992 | Okada et al. |
| 5,176,650 A | 1/1993 | Haining |
| 5,186,168 A | 2/1993 | Spofford et al. |
| 5,186,712 A | 2/1993 | Kelso et al. |
| 5,188,607 A | 2/1993 | Wu |
| 5,190,528 A | 3/1993 | Fonger et al. |
| 5,192,301 A | 3/1993 | Kamiya et al. |
| 5,195,974 A | 3/1993 | Hardy |
| 5,195,980 A | 3/1993 | Catlin |
| 5,195,985 A | 3/1993 | Hall |
| 5,205,830 A | 4/1993 | Dassa et al. |
| 5,215,527 A | 6/1993 | Beck et al. |
| 5,215,528 A | 6/1993 | Purdy et al. |
| 5,217,435 A | 6/1993 | Kring |
| 5,219,335 A | 6/1993 | Willard et al. |
| 5,221,255 A | 6/1993 | Mahurkar et al. |
| 5,222,944 A | 6/1993 | Harris |
| 5,225,369 A | 7/1993 | Su et al. |
| 5,226,899 A | 7/1993 | Lee et al. |
| D338,955 S | 8/1993 | Gresl et al. |
| 5,234,410 A | 8/1993 | Graham et al. |
| 5,242,411 A | 9/1993 | Yamamoto et al. |
| 5,246,426 A | 9/1993 | Lewis et al. |
| 5,246,430 A | 9/1993 | MacFarlane |
| 5,254,107 A | 10/1993 | Soltesz |
| 5,257,980 A | 11/1993 | Van Antwerp et al. |
| 5,267,982 A | 12/1993 | Sylvanowicz |
| 5,269,771 A | 12/1993 | Thomas et al. |
| D345,419 S | 3/1994 | Horrigan et al. |
| 5,290,310 A | 3/1994 | Makower et al. |
| 5,297,546 A | 3/1994 | Spofford et al. |
| 5,312,359 A | 5/1994 | Wallace |
| 5,312,361 A | 5/1994 | Zadini et al. |
| 5,312,363 A | 5/1994 | Ryan et al. |
| 5,320,608 A | 6/1994 | Gerrone |
| 5,322,517 A | 6/1994 | Sircom et al. |
| 5,330,435 A | 7/1994 | Vaillancourt |
| 5,334,159 A | 8/1994 | Turkel |
| 5,338,311 A | 8/1994 | Mahurkar |
| 5,352,205 A | 10/1994 | Dales et al. |
| 5,358,796 A | 10/1994 | Nakamura et al. |
| 5,366,441 A | 11/1994 | Crawford |
| 5,368,661 A | 11/1994 | Nakamura et al. |
| D353,668 S | 12/1994 | Banks et al. |
| 5,376,082 A | 12/1994 | Phelps |
| 5,376,094 A | 12/1994 | Kline |
| 5,380,290 A | 1/1995 | Makower et al. |
| 5,380,292 A | 1/1995 | Wilson |
| 5,395,341 A | 3/1995 | Slater |
| 5,397,311 A | 3/1995 | Walker et al. |
| 5,405,323 A | 4/1995 | Rogers et al. |
| 5,415,177 A | 5/1995 | Zadini et al. |
| 5,415,645 A | 5/1995 | Friend et al. |
| 5,419,766 A | 5/1995 | Chang et al. |
| 5,419,777 A | 5/1995 | Hofling |
| 5,423,760 A | 6/1995 | Yoon |
| 5,425,718 A | 6/1995 | Tay et al. |
| 5,431,506 A | 7/1995 | Masunaga |
| 5,445,625 A | 8/1995 | Voda |
| 5,454,785 A | 10/1995 | Smith |
| 5,454,790 A | 10/1995 | Dubrul |
| 5,456,258 A | 10/1995 | Kondo et al. |
| 5,456,668 A | 10/1995 | Ogle, II |
| 5,458,658 A | 10/1995 | Sircom |
| 5,466,230 A | 11/1995 | Davila |
| 5,480,389 A | 1/1996 | McWha et al. |
| 5,482,395 A | 1/1996 | Gasparini |
| 5,484,419 A | 1/1996 | Fleck |
| 5,487,734 A | 1/1996 | Thorne et al. |
| 5,489,273 A | 2/1996 | Whitney et al. |
| 5,496,281 A | 3/1996 | Krebs |
| 5,501,675 A | 3/1996 | Erskine |
| 5,507,300 A | 4/1996 | Mukai et al. |
| 5,512,052 A | 4/1996 | Jesch |
| 5,514,108 A | 5/1996 | Stevens |
| 5,520,655 A | 5/1996 | Davila et al. |
| 5,520,657 A * | 5/1996 | Sellers ............... A61M 25/06 600/575 |
| D371,195 S | 6/1996 | Krebs |
| 5,522,807 A | 6/1996 | Luther |
| 5,527,290 A | 6/1996 | Zadini et al. |
| 5,527,291 A | 6/1996 | Zadini et al. |
| 5,531,701 A | 7/1996 | Luther |
| 5,531,713 A | 7/1996 | Mastronardi et al. |
| 5,533,988 A | 7/1996 | Dickerson et al. |
| 5,535,785 A | 7/1996 | Werge et al. |
| 5,542,933 A | 8/1996 | Marks |
| 5,554,136 A | 9/1996 | Luther |
| 5,562,629 A | 10/1996 | Haughton et al. |
| 5,562,630 A | 10/1996 | Nichols |
| 5,562,631 A | 10/1996 | Bogert |
| 5,562,633 A | 10/1996 | Wozencroft et al. |
| 5,562,634 A | 10/1996 | Flumene et al. |
| 5,569,202 A | 10/1996 | Kovalic et al. |
| 5,569,217 A | 10/1996 | Luther |
| 5,571,073 A | 11/1996 | Castillo |
| 5,573,510 A | 11/1996 | Isaacson |
| 5,575,777 A | 11/1996 | Cover et al. |
| 5,591,194 A | 1/1997 | Berthiaume |
| 5,599,291 A | 2/1997 | Balbierz et al. |
| 5,599,327 A | 2/1997 | Sugahara et al. |
| 5,609,583 A | 3/1997 | Hakki et al. |
| 5,613,663 A | 3/1997 | Schmidt et al. |
| 5,613,954 A | 3/1997 | Nelson et al. |
| 5,630,802 A | 5/1997 | Moellmann et al. |
| 5,630,823 A | 5/1997 | Schmitz-Rode et al. |
| 5,634,475 A | 6/1997 | Wolvek |
| 5,634,913 A | 6/1997 | Stinger |
| 5,637,091 A | 6/1997 | Hakky et al. |
| 5,645,076 A | 7/1997 | Yoon |
| 5,651,772 A | 7/1997 | Arnett |
| D383,538 S | 9/1997 | Erskine et al. |
| 5,662,622 A | 9/1997 | Gore et al. |
| 5,674,241 A | 10/1997 | Bley et al. |
| 5,676,658 A | 10/1997 | Erskine |
| 5,683,368 A | 11/1997 | Schmidt |
| 5,683,370 A | 11/1997 | Luther et al. |
| 5,685,855 A | 11/1997 | Erskine |
| 5,685,858 A | 11/1997 | Kawand |
| 5,685,860 A | 11/1997 | Chang et al. |
| 5,688,249 A | 11/1997 | Chang et al. |
| 5,693,025 A | 12/1997 | Stevens |
| 5,695,474 A | 12/1997 | Daugherty |
| 5,700,250 A | 12/1997 | Erskine |
| 5,702,367 A | 12/1997 | Cover et al. |
| 5,702,369 A | 12/1997 | Mercereau |
| 5,704,914 A | 1/1998 | Stocking et al. |
| 5,722,425 A | 3/1998 | Bostrom |
| 5,725,503 A | 3/1998 | Arnett |
| 5,730,150 A | 3/1998 | Peppel et al. |
| 5,730,733 A | 3/1998 | Mortier et al. |
| 5,730,741 A | 3/1998 | Horzewski et al. |
| 5,738,144 A | 4/1998 | Rogers |
| 5,738,660 A | 4/1998 | Luther |
| 5,743,882 A | 4/1998 | Luther |
| 5,743,888 A | 4/1998 | Wilkes et al. |
| 5,749,371 A | 5/1998 | Zadini et al. |
| 5,749,857 A | 5/1998 | Cuppy |
| 5,749,861 A | 5/1998 | Guala et al. |
| 5,750,741 A | 5/1998 | Crocker et al. |
| 5,755,693 A | 5/1998 | Walker et al. |
| 5,755,709 A | 5/1998 | Cuppy |
| 5,762,630 A | 6/1998 | Bley et al. |
| 5,762,636 A | 6/1998 | Rupp et al. |
| 5,765,682 A | 6/1998 | Bley et al. |
| 5,779,679 A | 7/1998 | Shaw |
| 5,779,680 A | 7/1998 | Yoon |
| 5,779,681 A | 7/1998 | Bonn |
| 5,782,807 A | 7/1998 | Falvai et al. |
| D397,434 S | 8/1998 | Pike |
| 5,792,124 A | 8/1998 | Horrigan et al. |

(56) References Cited

U.S. PATENT DOCUMENTS

| | | |
|---|---|---|
| 5,800,395 A | 9/1998 | Botich et al. |
| 5,807,339 A | 9/1998 | Bostrom et al. |
| 5,807,342 A | 9/1998 | Musgrave et al. |
| 5,807,350 A | 9/1998 | Diaz |
| 5,810,835 A * | 9/1998 | Ryan ................ A61M 25/0084 604/159 |
| 5,813,411 A | 9/1998 | Van Bladel et al. |
| 5,817,058 A | 10/1998 | Shaw |
| 5,817,069 A | 10/1998 | Arnett |
| 5,824,001 A | 10/1998 | Erskine |
| 5,827,202 A | 10/1998 | Miraki et al. |
| 5,827,221 A | 10/1998 | Phelps |
| 5,827,227 A | 10/1998 | DeLago |
| 5,830,190 A | 11/1998 | Howell |
| 5,830,224 A | 11/1998 | Cohn et al. |
| 5,839,470 A | 11/1998 | Hiejima et al. |
| 5,843,038 A | 12/1998 | Bailey |
| 5,846,259 A | 12/1998 | Berthiaume |
| 5,851,196 A | 12/1998 | Arnett |
| 5,853,393 A | 12/1998 | Bogert |
| 5,855,615 A | 1/1999 | Bley et al. |
| 5,858,002 A | 1/1999 | Jesch |
| 5,865,806 A | 2/1999 | Howell |
| 5,873,864 A | 2/1999 | Luther et al. |
| 5,879,332 A | 3/1999 | Schwemberger et al. |
| 5,879,337 A | 3/1999 | Kuracina et al. |
| 5,885,217 A | 3/1999 | Gisselberg et al. |
| 5,885,251 A | 3/1999 | Luther |
| 5,891,098 A | 4/1999 | Huang |
| 5,891,105 A | 4/1999 | Mahurkar |
| 5,895,398 A | 4/1999 | Wensel et al. |
| 5,902,274 A | 5/1999 | Yamamoto et al. |
| 5,902,832 A | 5/1999 | Van Bladel et al. |
| 5,911,705 A | 6/1999 | Howell |
| 5,911,710 A | 6/1999 | Barry et al. |
| 5,913,848 A | 6/1999 | Luther et al. |
| 5,916,208 A | 6/1999 | Luther et al. |
| 5,928,199 A | 7/1999 | Nakagami |
| 5,935,110 A | 8/1999 | Brimhall |
| 5,941,854 A | 8/1999 | Bhitiyakul |
| 5,944,690 A | 8/1999 | Falwell et al. |
| 5,947,930 A | 9/1999 | Schwemberger et al. |
| 5,951,520 A | 9/1999 | Burzynski et al. |
| 5,954,698 A | 9/1999 | Pike |
| 5,957,893 A | 9/1999 | Luther et al. |
| 5,964,744 A | 10/1999 | Balbierz et al. |
| 5,967,490 A | 10/1999 | Pike |
| 5,984,895 A | 11/1999 | Padilla et al. |
| 5,984,903 A | 11/1999 | Nadal |
| 5,989,220 A | 11/1999 | Shaw et al. |
| 5,989,271 A | 11/1999 | Bonnette et al. |
| 5,997,507 A | 12/1999 | Dysarz |
| 5,997,510 A | 12/1999 | Schwemberger |
| 6,001,080 A | 12/1999 | Kuracina et al. |
| 6,004,278 A | 12/1999 | Botich et al. |
| 6,004,294 A | 12/1999 | Brimhall et al. |
| 6,004,295 A | 12/1999 | Langer et al. |
| 6,011,988 A | 1/2000 | Lynch et al. |
| 6,019,736 A | 2/2000 | Avellanet et al. |
| 6,022,319 A | 2/2000 | Willard et al. |
| 6,024,727 A | 2/2000 | Thorne et al. |
| 6,024,729 A | 2/2000 | Dehdashtian et al. |
| 6,045,734 A | 4/2000 | Luther et al. |
| 6,056,726 A | 5/2000 | Isaacson |
| 6,066,100 A | 5/2000 | Willard et al. |
| 6,074,378 A | 6/2000 | Mouri et al. |
| 6,077,244 A | 6/2000 | Botich et al. |
| 6,080,137 A | 6/2000 | Pike |
| 6,083,237 A | 7/2000 | Huitema et al. |
| 6,096,004 A | 8/2000 | Meglan et al. |
| 6,096,005 A | 8/2000 | Botich et al. |
| 6,117,108 A | 9/2000 | Woehr et al. |
| 6,120,494 A | 9/2000 | Jonkman |
| 6,126,641 A | 10/2000 | Shields |
| 6,139,532 A | 10/2000 | Howell et al. |
| 6,139,557 A | 10/2000 | Passafaro et al. |
| 6,159,179 A | 12/2000 | Simonson |
| 6,171,234 B1 | 1/2001 | White et al. |
| 6,171,287 B1 | 1/2001 | Lynn et al. |
| 6,176,842 B1 | 1/2001 | Tachibana et al. |
| 6,193,690 B1 | 2/2001 | Dysarz |
| 6,197,001 B1 | 3/2001 | Wilson et al. |
| 6,197,007 B1 | 3/2001 | Thorne et al. |
| 6,197,041 B1 | 3/2001 | Shichman et al. |
| 6,203,527 B1 | 3/2001 | Zadini et al. |
| 6,213,978 B1 | 4/2001 | Voyten |
| 6,217,558 B1 | 4/2001 | Zadini et al. |
| 6,221,047 B1 | 4/2001 | Green et al. |
| 6,221,048 B1 | 4/2001 | Phelps |
| 6,221,049 B1 | 4/2001 | Selmon et al. |
| 6,224,569 B1 | 5/2001 | Brimhall |
| 6,228,060 B1 | 5/2001 | Howell |
| 6,228,062 B1 | 5/2001 | Howell et al. |
| 6,228,073 B1 | 5/2001 | Noone et al. |
| 6,245,045 B1 | 6/2001 | Stratienko |
| 6,251,092 B1 | 6/2001 | Qin et al. |
| 6,268,399 B1 | 7/2001 | Hultine et al. |
| 6,270,480 B1 | 8/2001 | Dorr et al. |
| 6,273,871 B1 | 8/2001 | Davis et al. |
| 6,280,419 B1 | 8/2001 | Vojtasek |
| 6,287,278 B1 | 9/2001 | Woehr et al. |
| 6,309,379 B1 | 10/2001 | Willard et al. |
| 6,319,244 B2 | 11/2001 | Suresh et al. |
| 6,322,537 B1 | 11/2001 | Chang |
| D452,003 S | 12/2001 | Niermann |
| 6,325,781 B1 | 12/2001 | Takagi et al. |
| 6,325,797 B1 | 12/2001 | Stewart et al. |
| 6,336,914 B1 | 1/2002 | Gillespie, III |
| 6,352,520 B1 | 3/2002 | Miyazaki et al. |
| 6,368,337 B1 | 4/2002 | Kieturakis et al. |
| 6,379,333 B1 | 4/2002 | Brimhall et al. |
| 6,379,372 B1 | 4/2002 | Dehdashtian et al. |
| D457,955 S | 5/2002 | Bilitz |
| 6,406,442 B1 | 6/2002 | McFann et al. |
| D460,179 S | 7/2002 | Isoda et al. |
| 6,422,989 B1 | 7/2002 | Hektner |
| 6,436,070 B1 | 8/2002 | Botich et al. |
| 6,436,112 B2 | 8/2002 | Wensel et al. |
| 6,443,929 B1 | 9/2002 | Kuracina et al. |
| 6,451,052 B1 | 9/2002 | Burmeister et al. |
| 6,461,362 B1 | 10/2002 | Halseth et al. |
| 6,475,217 B1 | 11/2002 | Platt |
| 6,478,779 B1 | 11/2002 | Hu |
| 6,485,473 B1 | 11/2002 | Lynn |
| 6,485,497 B2 | 11/2002 | Wensel et al. |
| 6,497,681 B1 | 12/2002 | Brenner |
| 6,506,181 B2 | 1/2003 | Meng et al. |
| 6,514,236 B1 | 2/2003 | Stratienko |
| 6,524,276 B1 | 2/2003 | Halseth et al. |
| D471,980 S | 3/2003 | Caizza |
| 6,527,759 B1 | 3/2003 | Tachibana et al. |
| 6,530,913 B1 | 3/2003 | Giba et al. |
| 6,530,935 B2 | 3/2003 | Wensel et al. |
| 6,540,725 B1 | 4/2003 | Ponzi |
| 6,540,732 B1 | 4/2003 | Botich et al. |
| 6,544,239 B2 | 4/2003 | Kinsey et al. |
| 6,547,762 B1 | 4/2003 | Botich et al. |
| 6,558,355 B1 | 5/2003 | Metzger et al. |
| 6,582,402 B1 | 6/2003 | Erskine |
| 6,582,440 B1 | 6/2003 | Brumbach |
| 6,585,703 B1 | 7/2003 | Kassel et al. |
| 6,589,262 B1 | 7/2003 | Honebrink et al. |
| 6,595,955 B2 | 7/2003 | Ferguson et al. |
| 6,595,959 B1 | 7/2003 | Stratienko |
| 6,607,511 B2 | 8/2003 | Halseth et al. |
| 6,616,630 B1 | 9/2003 | Woehr et al. |
| 6,620,136 B1 | 9/2003 | Pressly, Sr. et al. |
| 6,623,449 B2 | 9/2003 | Paskar |
| 6,626,868 B1 | 9/2003 | Prestidge et al. |
| 6,626,869 B1 | 9/2003 | Bint |
| 6,629,959 B2 | 10/2003 | Kuracina et al. |
| 6,632,201 B1 | 10/2003 | Mathias et al. |
| 6,638,252 B2 | 10/2003 | Moulton et al. |
| 6,641,564 B1 | 11/2003 | Kraus |

(56) References Cited

U.S. PATENT DOCUMENTS

| | | | |
|---|---|---|---|
| 6,645,178 B1 | 11/2003 | Junker et al. |
| 6,652,486 B2 | 11/2003 | Bialecki et al. |
| 6,652,490 B2 | 11/2003 | Howell |
| 6,663,577 B2 | 12/2003 | Jen et al. |
| 6,663,592 B2 | 12/2003 | Rhad et al. |
| 6,666,865 B2 | 12/2003 | Platt |
| 6,679,900 B2 | 1/2004 | Kieturakis et al. |
| 6,689,102 B2 | 2/2004 | Greene |
| 6,692,508 B2 | 2/2004 | Wensel et al. |
| 6,692,509 B2 | 2/2004 | Wensel et al. |
| 6,695,814 B2 | 2/2004 | Greene et al. |
| 6,695,856 B2 | 2/2004 | Kieturakis et al. |
| 6,695,860 B1 | 2/2004 | Ward et al. |
| 6,699,221 B2 | 3/2004 | Vaillancourt |
| 6,702,811 B2 | 3/2004 | Stewart et al. |
| 6,706,018 B2 | 3/2004 | Westlund et al. |
| 6,711,444 B2 | 3/2004 | Koblish |
| 6,712,790 B1 | 3/2004 | Prestidge et al. |
| 6,712,797 B1 | 3/2004 | Southern, Jr. |
| 6,716,197 B2 | 4/2004 | Svendsen |
| 6,730,062 B2 | 5/2004 | Hoffman et al. |
| 6,740,063 B2 | 5/2004 | Lynn |
| 6,740,096 B2 | 5/2004 | Teague et al. |
| 6,745,080 B2 | 6/2004 | Koblish |
| 6,749,588 B1 | 6/2004 | Howell et al. |
| 6,764,468 B1 | 7/2004 | East |
| D494,270 S | 8/2004 | Reschke |
| 6,776,788 B1 | 8/2004 | Klint et al. |
| 6,796,962 B2 | 9/2004 | Ferguson et al. |
| 6,824,545 B2 | 11/2004 | Sepetka et al. |
| 6,832,715 B2 | 12/2004 | Eungard et al. |
| 6,835,190 B2 | 12/2004 | Nguyen |
| 6,837,867 B2 | 1/2005 | Kortelling |
| 6,860,871 B2 | 3/2005 | Kuracina et al. |
| 6,872,193 B2 | 3/2005 | Shaw et al. |
| 6,887,220 B2 | 5/2005 | Hogendijk |
| 6,902,546 B2 | 6/2005 | Ferguson |
| 6,905,483 B2 | 6/2005 | Newby et al. |
| 6,913,595 B2 | 7/2005 | Mastorakis |
| 6,916,311 B2 | 7/2005 | Vojtasek |
| 6,921,386 B2 | 7/2005 | Shue et al. |
| 6,921,391 B1 | 7/2005 | Barker et al. |
| 6,929,624 B1 * | 8/2005 | Del Castillo ..... A61M 25/0631 604/164.07 |
| 6,939,325 B2 | 9/2005 | Haining |
| 6,942,652 B1 | 9/2005 | Pressly, Sr. et al. |
| 6,953,448 B2 | 10/2005 | Moulton et al. |
| 6,958,054 B2 | 10/2005 | Fitzgerald |
| 6,958,055 B2 | 10/2005 | Donnan et al. |
| 6,960,191 B2 | 11/2005 | Howlett et al. |
| 6,972,002 B2 | 12/2005 | Thorne |
| 6,974,438 B2 | 12/2005 | Shekalim |
| 6,994,693 B2 | 2/2006 | Tal |
| 7,001,396 B2 | 2/2006 | Glazier et al. |
| 7,004,927 B2 | 2/2006 | Ferguson et al. |
| 7,008,404 B2 | 3/2006 | Nakajima |
| 7,018,372 B2 | 3/2006 | Casey et al. |
| 7,018,390 B2 | 3/2006 | Turovskiy et al. |
| 7,025,746 B2 | 4/2006 | Tal |
| 7,029,467 B2 | 4/2006 | Currier et al. |
| 7,033,335 B2 | 4/2006 | Haarala et al. |
| 7,044,935 B2 | 5/2006 | Shue et al. |
| 7,060,055 B2 | 6/2006 | Wilkinson et al. |
| 7,090,656 B1 | 8/2006 | Botich et al. |
| 7,094,243 B2 | 8/2006 | Mulholland et al. |
| 7,097,633 B2 | 8/2006 | Botich et al. |
| 7,125,396 B2 | 10/2006 | Leinsing et al. |
| 7,125,397 B2 | 10/2006 | Woehr et al. |
| 7,141,040 B2 | 11/2006 | Lichtenberg |
| 7,153,276 B2 | 12/2006 | Barker et al. |
| 7,163,520 B2 | 1/2007 | Bernard et al. |
| 7,169,159 B2 | 1/2007 | Green et al. |
| 7,179,244 B2 | 2/2007 | Smith et al. |
| 7,186,239 B2 | 3/2007 | Woehr |
| 7,191,900 B2 | 3/2007 | Opie et al. |
| 7,192,433 B2 | 3/2007 | Osypka et al. |
| 7,204,813 B2 | 4/2007 | Shue et al. |
| 7,214,211 B2 | 5/2007 | Woehr et al. |
| 7,264,613 B2 | 9/2007 | Woehr et al. |
| 7,291,130 B2 | 11/2007 | McGurk |
| 7,303,547 B2 | 12/2007 | Pressly, Sr. et al. |
| 7,303,548 B2 | 12/2007 | Rhad et al. |
| 7,314,462 B2 | 1/2008 | O'Reagan et al. |
| 7,331,966 B2 | 2/2008 | Soma et al. |
| 7,344,516 B2 | 3/2008 | Erskine |
| 7,354,422 B2 | 4/2008 | Riesenberger et al. |
| 7,374,554 B2 | 5/2008 | Menzi et al. |
| 7,381,205 B2 | 6/2008 | Thommen |
| 7,396,346 B2 | 7/2008 | Nakajima |
| 7,413,562 B2 | 8/2008 | Ferguson et al. |
| 7,422,572 B2 | 9/2008 | Popov et al. |
| 7,458,954 B2 | 12/2008 | Ferguson et al. |
| 7,465,294 B1 | 12/2008 | Vladimirsky |
| 7,468,057 B2 | 12/2008 | Ponzi |
| 7,470,254 B2 | 12/2008 | Basta et al. |
| 7,491,176 B2 | 2/2009 | Mann |
| 7,494,010 B2 | 2/2009 | Opie et al. |
| 7,500,965 B2 | 3/2009 | Menzi et al. |
| 7,507,222 B2 | 3/2009 | Cindrich et al. |
| 7,513,887 B2 | 4/2009 | Halseth et al. |
| 7,513,888 B2 | 4/2009 | Sircom et al. |
| 7,524,306 B2 | 4/2009 | Botich et al. |
| 7,530,965 B2 | 5/2009 | Villa et al. |
| 7,534,227 B2 | 5/2009 | Kulli |
| 7,534,231 B2 | 5/2009 | Kuracina et al. |
| 7,544,170 B2 | 6/2009 | Williams et al. |
| 7,556,617 B2 | 7/2009 | Voorhees, Jr. et al. |
| 7,566,323 B2 | 7/2009 | Chang |
| D601,243 S | 9/2009 | Bierman et al. |
| 7,597,681 B2 | 10/2009 | Sutton et al. |
| 7,608,057 B2 | 10/2009 | Woehr et al. |
| D604,839 S | 11/2009 | Crawford et al. |
| 7,611,485 B2 | 11/2009 | Ferguson |
| 7,611,487 B2 | 11/2009 | Woehr et al. |
| 7,611,499 B2 | 11/2009 | Woehr et al. |
| 7,618,395 B2 | 11/2009 | Ferguson |
| 7,625,360 B2 | 12/2009 | Woehr et al. |
| 7,628,769 B2 | 12/2009 | Grandt et al. |
| 7,632,243 B2 | 12/2009 | Bialecki et al. |
| 7,645,263 B2 | 1/2010 | Angel et al. |
| 7,654,988 B2 | 2/2010 | Moulton et al. |
| 7,658,725 B2 | 2/2010 | Bialecki et al. |
| D612,043 S | 3/2010 | Young et al. |
| 7,678,080 B2 | 3/2010 | Shue et al. |
| 7,682,358 B2 | 3/2010 | Gullickson et al. |
| 7,691,088 B2 | 4/2010 | Howell |
| 7,691,090 B2 | 4/2010 | Belley et al. |
| 7,691,093 B2 | 4/2010 | Brimhall |
| 7,695,458 B2 | 4/2010 | Belley et al. |
| 7,699,807 B2 | 4/2010 | Faust et al. |
| D615,197 S | 5/2010 | Koh et al. |
| 7,708,721 B2 | 5/2010 | Khaw |
| 7,713,243 B2 | 5/2010 | Hillman |
| 7,717,875 B2 | 5/2010 | Knudson et al. |
| 7,722,567 B2 | 5/2010 | Tal |
| 7,722,569 B2 | 5/2010 | Soderholm et al. |
| D617,893 S | 6/2010 | Bierman et al. |
| 7,731,687 B2 | 6/2010 | Menzi et al. |
| 7,731,691 B2 | 6/2010 | Cote et al. |
| 7,736,332 B2 | 6/2010 | Carlyon et al. |
| 7,736,337 B2 | 6/2010 | Diep et al. |
| 7,736,339 B2 | 6/2010 | Woehr et al. |
| 7,736,342 B2 | 6/2010 | Abriles et al. |
| 7,740,615 B2 | 6/2010 | Shaw et al. |
| 7,744,574 B2 | 6/2010 | Pederson et al. |
| 7,753,877 B2 | 7/2010 | Bialecki et al. |
| 7,753,887 B2 | 7/2010 | Botich et al. |
| 7,762,984 B2 | 7/2010 | Kumoyama et al. |
| 7,762,993 B2 | 7/2010 | Perez |
| 7,766,879 B2 | 8/2010 | Tan et al. |
| 7,776,052 B2 | 8/2010 | Greenberg et al. |
| 7,785,296 B2 | 8/2010 | Muskatello et al. |
| 7,794,424 B2 | 9/2010 | Paskar |
| 7,798,994 B2 | 9/2010 | Brimhall |

(56) References Cited

U.S. PATENT DOCUMENTS

| | | |
|---|---|---|
| 7,803,142 B2 | 9/2010 | Longson et al. |
| 7,828,773 B2 | 11/2010 | Swisher et al. |
| 7,828,774 B2 | 11/2010 | Harding et al. |
| 7,850,644 B2 | 12/2010 | Gonzalez et al. |
| D634,843 S | 3/2011 | Kim et al. |
| 7,896,862 B2 | 3/2011 | Long et al. |
| 7,905,857 B2 | 3/2011 | Swisher |
| 7,914,488 B2 | 3/2011 | Dickerson |
| 7,914,492 B2 | 3/2011 | Heuser |
| 7,922,696 B2 | 4/2011 | Tal et al. |
| 7,922,698 B2 | 4/2011 | Riesenberger et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 7,972,313 B2 | 7/2011 | Woehr et al. |
| 7,972,324 B2 | 7/2011 | Quint |
| 8,029,470 B2 | 10/2011 | Whiting et al. |
| 8,029,472 B2 | 10/2011 | Leinsing et al. |
| 8,048,031 B2 | 11/2011 | Shaw et al. |
| 8,048,039 B2 | 11/2011 | Carlyon et al. |
| 8,057,404 B2 | 11/2011 | Fujiwara et al. |
| 8,062,261 B2 | 11/2011 | Adams |
| 8,075,529 B2 | 12/2011 | Nakajima et al. |
| 8,079,979 B2 | 12/2011 | Moorehead |
| D653,329 S | 1/2012 | Lee-Sepsick |
| 8,100,858 B2 | 1/2012 | Woehr et al. |
| 8,105,286 B2 | 1/2012 | Anderson et al. |
| 8,105,315 B2 | 1/2012 | Johnson et al. |
| 8,123,727 B2 | 2/2012 | Luther et al. |
| 8,152,758 B2 | 4/2012 | Chan et al. |
| 8,162,881 B2 | 4/2012 | Lilley, Jr. et al. |
| 8,167,851 B2 | 5/2012 | Sen |
| 8,177,753 B2 | 5/2012 | Vitullo et al. |
| RE43,473 E | 6/2012 | Newby et al. |
| 8,192,402 B2 | 6/2012 | Anderson et al. |
| 8,202,251 B2 | 6/2012 | Bierman et al. |
| 8,202,253 B1 | 6/2012 | Wexler |
| 8,206,343 B2 | 6/2012 | Racz |
| 8,211,070 B2 | 7/2012 | Woehr et al. |
| 8,221,387 B2 | 7/2012 | Shelso et al. |
| 8,226,612 B2 | 7/2012 | Nakajima |
| 8,235,945 B2 | 8/2012 | Baid |
| 8,251,923 B2 | 8/2012 | Carrez et al. |
| 8,251,950 B2 | 8/2012 | Albert et al. |
| D667,111 S | 9/2012 | Robinson |
| 8,257,322 B2 | 9/2012 | Koehler et al. |
| 8,273,054 B2 | 9/2012 | St. Germain et al. |
| 8,286,657 B2 | 10/2012 | Belley et al. |
| 8,298,186 B2 | 10/2012 | Popov |
| 8,303,543 B2 | 11/2012 | Abulhaj |
| 8,308,685 B2 | 11/2012 | Botich et al. |
| 8,308,691 B2 | 11/2012 | Woehr et al. |
| D672,456 S | 12/2012 | Lee-Sepsick |
| 8,328,762 B2 | 12/2012 | Woehr et al. |
| 8,328,837 B2 | 12/2012 | Binmoeller |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,337,471 B2 | 12/2012 | Baid |
| D675,318 S | 1/2013 | Luk et al. |
| 8,361,020 B2 | 1/2013 | Stout |
| 8,361,038 B2 | 1/2013 | McKinnon et al. |
| 8,376,994 B2 | 2/2013 | Woehr et al. |
| 8,377,006 B2 | 2/2013 | Tal et al. |
| 8,382,721 B2 | 2/2013 | Woehr et al. |
| 8,388,583 B2 | 3/2013 | Stout et al. |
| 8,403,886 B2 | 3/2013 | Bialecki et al. |
| 8,412,300 B2 | 4/2013 | Sonderegger |
| 8,414,539 B1 | 4/2013 | Kuracina et al. |
| 8,419,688 B2 | 4/2013 | Woehr et al. |
| 8,444,605 B2 | 5/2013 | Kuracina et al. |
| 8,454,536 B2 | 6/2013 | Raulerson et al. |
| 8,460,247 B2 | 6/2013 | Woehr et al. |
| 8,469,928 B2 | 6/2013 | Stout et al. |
| 8,496,628 B2 | 7/2013 | Erskine |
| D687,548 S | 8/2013 | Hayashi |
| 8,506,533 B2 | 8/2013 | Carlyon et al. |
| 8,509,340 B2 | 8/2013 | Michelitsch |
| 8,517,959 B2 | 8/2013 | Kurosawa et al. |
| 8,529,515 B2 | 9/2013 | Woehr et al. |
| 8,535,271 B2 | 9/2013 | Fuchs et al. |
| 8,540,728 B2 | 9/2013 | Woehr et al. |
| 8,545,454 B2 | 10/2013 | Kuracina et al. |
| 8,568,372 B2 | 10/2013 | Woehr et al. |
| 8,574,203 B2 | 11/2013 | Stout et al. |
| 8,585,660 B2 | 11/2013 | Murphy |
| 8,591,467 B2 | 11/2013 | Walker et al. |
| 8,591,468 B2 | 11/2013 | Woehr et al. |
| 8,597,249 B2 | 12/2013 | Woehr et al. |
| 8,622,931 B2 | 1/2014 | Teague et al. |
| 8,622,972 B2 | 1/2014 | Nystrom et al. |
| D700,318 S | 2/2014 | Amoah et al. |
| 8,647,301 B2 | 2/2014 | Bialecki et al. |
| 8,647,313 B2 | 2/2014 | Woehr et al. |
| 8,647,324 B2 | 2/2014 | DeLegge et al. |
| 8,652,104 B2 | 2/2014 | Goral et al. |
| 8,657,790 B2 | 2/2014 | Tal et al. |
| 8,672,888 B2 | 3/2014 | Tal |
| 8,679,063 B2 | 3/2014 | Stout et al. |
| 8,690,833 B2 | 4/2014 | Belson |
| 8,715,242 B2 | 5/2014 | Helm, Jr. |
| 8,721,546 B2 | 5/2014 | Belson |
| 8,728,030 B2 | 5/2014 | Woehr |
| 8,728,035 B2 | 5/2014 | Warring et al. |
| 8,740,859 B2 | 6/2014 | McKinnon et al. |
| 8,740,964 B2 | 6/2014 | Hartley |
| 8,747,387 B2 | 6/2014 | Belley et al. |
| 8,753,317 B2 | 6/2014 | Osborne et al. |
| 8,764,711 B2 | 7/2014 | Kuracina et al. |
| D710,495 S | 8/2014 | Wu et al. |
| 8,814,833 B2 | 8/2014 | Farrell et al. |
| D713,957 S | 9/2014 | Woehr et al. |
| D714,436 S | 9/2014 | Lee-Sepsick |
| 8,827,965 B2 | 9/2014 | Woehr et al. |
| 8,845,584 B2 | 9/2014 | Ferguson et al. |
| D715,931 S | 10/2014 | Watanabe et al. |
| 8,864,714 B2 | 10/2014 | Harding et al. |
| 8,900,192 B2 | 12/2014 | Anderson et al. |
| 8,932,257 B2 | 1/2015 | Woehr |
| 8,932,258 B2 | 1/2015 | Blanchard et al. |
| 8,932,259 B2 | 1/2015 | Stout et al. |
| 8,951,230 B2 | 2/2015 | Tanabe et al. |
| 8,956,327 B2 | 2/2015 | Bierman et al. |
| 8,974,426 B2 | 3/2015 | Corcoran et al. |
| 8,979,802 B2 | 3/2015 | Woehr |
| 8,986,227 B2 | 3/2015 | Belson |
| D726,908 S | 4/2015 | Yu et al. |
| 8,998,852 B2 | 4/2015 | Blanchard et al. |
| 9,005,169 B2 | 4/2015 | Gravesen et al. |
| 9,011,351 B2 | 4/2015 | Hoshinouchi |
| 9,011,381 B2 | 4/2015 | Yamada et al. |
| D728,781 S | 5/2015 | Pierson et al. |
| 9,022,979 B2 | 5/2015 | Woehr |
| 9,033,927 B2 | 5/2015 | Maan et al. |
| D733,289 S | 6/2015 | Blanchard et al. |
| 9,044,583 B2 | 6/2015 | Vaillancourt |
| D735,321 S | 7/2015 | Blanchard |
| 9,089,671 B2 | 7/2015 | Stout et al. |
| 9,095,683 B2 | 8/2015 | Hall et al. |
| 9,101,746 B2 | 8/2015 | Stout et al. |
| 9,108,021 B2 | 8/2015 | Hyer et al. |
| 9,114,231 B2 | 8/2015 | Woehr et al. |
| 9,114,241 B2 | 8/2015 | Stout et al. |
| 9,126,012 B2 | 9/2015 | McKinnon et al. |
| 9,138,252 B2 | 9/2015 | Bierman et al. |
| 9,138,545 B2 | 9/2015 | Shaw et al. |
| 9,138,559 B2 | 9/2015 | Odland et al. |
| RE45,776 E | 10/2015 | Root et al. |
| D740,410 S | 10/2015 | Korkuch et al. |
| 9,149,625 B2 | 10/2015 | Woehr et al. |
| 9,149,626 B2 | 10/2015 | Woehr et al. |
| 9,155,863 B2 | 10/2015 | Isaacson et al. |
| 9,162,036 B2 | 10/2015 | Caples et al. |
| 9,162,037 B2 | 10/2015 | Belson et al. |

(56) References Cited

U.S. PATENT DOCUMENTS

| | | |
|---|---|---|
| 9,180,275 B2 | 11/2015 | Helm |
| D746,445 S | 12/2015 | Lazarus |
| 9,205,231 B2 | 12/2015 | Call et al. |
| 9,216,109 B2 | 12/2015 | Badawi et al. |
| 9,220,531 B2 | 12/2015 | Datta et al. |
| 9,220,871 B2 | 12/2015 | Thorne et al. |
| 9,220,882 B2 | 12/2015 | Belley et al. |
| D748,254 S | 1/2016 | Freigang et al. |
| 9,227,038 B2 | 1/2016 | Woehr |
| 9,242,071 B2 | 1/2016 | Morgan et al. |
| 9,242,072 B2 | 1/2016 | Morgan et al. |
| RE45,896 E | 2/2016 | Stout et al. |
| D748,774 S | 2/2016 | Caron |
| D748,777 S | 2/2016 | Uenishi et al. |
| D749,214 S | 2/2016 | Uenishi et al. |
| D749,727 S | 2/2016 | Wapler et al. |
| D751,194 S | 3/2016 | Yu et al. |
| D752,737 S | 3/2016 | Ohashi |
| 9,289,237 B2 | 3/2016 | Woehr et al. |
| 9,308,352 B2 | 4/2016 | Teoh et al. |
| 9,308,354 B2 | 4/2016 | Farrell et al. |
| 9,320,870 B2 | 4/2016 | Woehr |
| D755,368 S | 5/2016 | Efinger et al. |
| 9,352,119 B2 | 5/2016 | Burkholz et al. |
| 9,352,127 B2 | 5/2016 | Yeh et al. |
| 9,352,129 B2 | 5/2016 | Nardeo et al. |
| 9,358,364 B2 | 6/2016 | Isaacson et al. |
| 9,370,641 B2 | 6/2016 | Woehr et al. |
| 9,381,324 B2 | 7/2016 | Fuchs et al. |
| 9,399,116 B2 | 7/2016 | Goral et al. |
| 9,408,569 B2 | 8/2016 | Andreae et al. |
| 9,421,345 B2 | 8/2016 | Woehr et al. |
| 9,427,549 B2 | 8/2016 | Woehr et al. |
| 9,522,254 B2 | 12/2016 | Belson |
| 9,545,495 B2 | 1/2017 | Goral et al. |
| 9,579,486 B2 | 2/2017 | Burkholz et al. |
| 9,586,027 B2 | 3/2017 | Tisci et al. |
| 9,592,367 B2 | 3/2017 | Harding et al. |
| 9,616,201 B2 | 4/2017 | Belson |
| 9,623,210 B2 | 4/2017 | Woehr |
| 9,675,784 B2 | 6/2017 | Belson |
| 9,687,633 B2 | 6/2017 | Teoh |
| 9,707,378 B2 | 7/2017 | Leinsing et al. |
| 9,717,523 B2 | 8/2017 | Feng et al. |
| 9,717,887 B2 | 8/2017 | Tan |
| 9,737,252 B2 | 8/2017 | Teoh et al. |
| 9,750,532 B2 | 9/2017 | Toomey et al. |
| 9,750,928 B2 | 9/2017 | Burkholz et al. |
| 9,757,540 B2 | 9/2017 | Belson |
| 9,764,085 B2 | 9/2017 | Teoh |
| 9,764,117 B2 | 9/2017 | Bierman et al. |
| 9,775,972 B2 | 10/2017 | Christensen et al. |
| 9,782,568 B2 | 10/2017 | Belson |
| 9,789,279 B2 | 10/2017 | Burkholz et al. |
| 9,795,766 B2 | 10/2017 | Teoh |
| 9,844,646 B2 | 12/2017 | Knutsson |
| 9,861,792 B2 | 1/2018 | Hall et al. |
| 9,872,971 B2 | 1/2018 | Blanchard |
| 9,950,139 B2 | 4/2018 | Blanchard et al. |
| 9,962,525 B2 | 5/2018 | Woehr |
| 10,004,878 B2 | 6/2018 | Ishida |
| 10,086,171 B2 | 10/2018 | Belson |
| 10,232,146 B2 | 3/2019 | Braithwaite et al. |
| 2001/0014786 A1 | 8/2001 | Greene et al. |
| 2001/0020153 A1 | 9/2001 | Howell |
| 2002/0052576 A1 | 5/2002 | Massengale |
| 2002/0077595 A1 | 6/2002 | Hundertmark et al. |
| 2002/0103446 A1 | 8/2002 | McFann et al. |
| 2002/0107526 A1 | 8/2002 | Greenberg et al. |
| 2002/0128604 A1 | 9/2002 | Nakajima |
| 2002/0165497 A1 | 11/2002 | Greene |
| 2002/0177812 A1 | 11/2002 | Moulton et al. |
| 2003/0032922 A1 | 2/2003 | Moorehead |
| 2003/0032936 A1 | 2/2003 | Lederman |
| 2003/0060760 A1 | 3/2003 | Botich et al. |
| 2003/0073956 A1 | 4/2003 | Hoffman et al. |
| 2003/0120214 A1 | 6/2003 | Howell |
| 2003/0153874 A1 | 8/2003 | Tal |
| 2003/0187396 A1 | 10/2003 | Ponzi |
| 2003/0204186 A1 | 10/2003 | Geistert |
| 2004/0019329 A1 | 1/2004 | Erskine |
| 2004/0034383 A1 | 2/2004 | Belson |
| 2004/0044302 A1 | 3/2004 | Bernard et al. |
| 2004/0044313 A1 | 3/2004 | Nakajima |
| 2004/0092879 A1 | 5/2004 | Kraus et al. |
| 2004/0106903 A1 | 6/2004 | Shue et al. |
| 2004/0111059 A1* | 6/2004 | Howlett ............ A61M 25/0606 604/164.13 |
| 2004/0122373 A1 | 6/2004 | Botich et al. |
| 2004/0176758 A1 | 9/2004 | Yassinzadeh |
| 2004/0193118 A1 | 9/2004 | Bergeron |
| 2004/0215146 A1 | 10/2004 | Lampropoulos et al. |
| 2004/0236288 A1 | 11/2004 | Howell et al. |
| 2004/0243061 A1 | 12/2004 | McGurk |
| 2004/0267204 A1 | 12/2004 | Brustowicz |
| 2005/0004524 A1 | 1/2005 | Newby et al. |
| 2005/0010095 A1 | 1/2005 | Stewart et al. |
| 2005/0020940 A1 | 1/2005 | Opie et al. |
| 2005/0027256 A1 | 2/2005 | Barker et al. |
| 2005/0033137 A1 | 2/2005 | Oral et al. |
| 2005/0040061 A1 | 2/2005 | Opie et al. |
| 2005/0075606 A1* | 4/2005 | Botich ............ A61M 25/0631 604/110 |
| 2005/0107769 A1 | 5/2005 | Thommen |
| 2005/0119619 A1 | 6/2005 | Haining |
| 2005/0131350 A1 | 6/2005 | Shaw et al. |
| 2005/0165355 A1 | 7/2005 | Fitzgerald |
| 2005/0197623 A1 | 9/2005 | Leeflang et al. |
| 2005/0245847 A1* | 11/2005 | Schaeffer ........ A61M 25/09041 600/585 |
| 2005/0256505 A1 | 11/2005 | Long et al. |
| 2005/0273057 A1 | 12/2005 | Popov |
| 2006/0025721 A1 | 2/2006 | Duffy et al. |
| 2006/0079787 A1 | 4/2006 | Whiting et al. |
| 2006/0084964 A1 | 4/2006 | Knudson et al. |
| 2006/0155245 A1 | 7/2006 | Woehr |
| 2006/0161115 A1 | 7/2006 | Fangrow |
| 2006/0167405 A1 | 7/2006 | King et al. |
| 2006/0200080 A1 | 9/2006 | Abulhaj |
| 2006/0229563 A1 | 10/2006 | O'Reagan et al. |
| 2006/0264834 A1 | 11/2006 | Vaillancourt |
| 2007/0043422 A1 | 2/2007 | Shmulewitz et al. |
| 2007/0060999 A1 | 3/2007 | Randall et al. |
| 2007/0083162 A1 | 4/2007 | O'Reagan et al. |
| 2007/0083188 A1 | 4/2007 | Grandt et al. |
| 2007/0100284 A1 | 5/2007 | Leinsing et al. |
| 2007/0123803 A1 | 5/2007 | Fujiwara et al. |
| 2007/0142779 A1 | 6/2007 | Duane et al. |
| 2007/0179446 A1 | 8/2007 | Carrez et al. |
| 2007/0191777 A1 | 8/2007 | King |
| 2007/0193903 A1 | 8/2007 | Opie et al. |
| 2007/0225647 A1 | 9/2007 | Luther et al. |
| 2007/0233007 A1 | 10/2007 | Adams |
| 2007/0244438 A1 | 10/2007 | Perez |
| 2007/0255221 A1 | 11/2007 | Nakajima |
| 2007/0276288 A1 | 11/2007 | Khaw |
| 2008/0039796 A1 | 2/2008 | Nakajima |
| 2008/0082082 A1 | 4/2008 | Carlyon et al. |
| 2008/0097330 A1 | 4/2008 | King et al. |
| 2008/0108911 A1 | 5/2008 | Palmer |
| 2008/0108944 A1 | 5/2008 | Woehr et al. |
| 2008/0108974 A1 | 5/2008 | Yee Roth |
| 2008/0125709 A1 | 5/2008 | Chang et al. |
| 2008/0131300 A1 | 6/2008 | Junod et al. |
| 2008/0132846 A1 | 6/2008 | Shue et al. |
| 2008/0147010 A1 | 6/2008 | Nakajima et al. |
| 2008/0243165 A1 | 10/2008 | Mauch et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0300574 A1* | 12/2008 | Belson ............ A61M 25/0606 604/510 |
| 2009/0030380 A1 | 1/2009 | Binmoeller |
| 2009/0036836 A1 | 2/2009 | Nystrom et al. |

(56) References Cited

U.S. PATENT DOCUMENTS

| | | |
|---|---|---|
| 2009/0048566 A1 | 2/2009 | Ferguson et al. |
| 2009/0131872 A1 | 5/2009 | Popov |
| 2009/0157006 A1 | 6/2009 | Nardeo et al. |
| 2009/0221961 A1 | 9/2009 | Tal et al. |
| 2009/0292243 A1 | 11/2009 | Harding et al. |
| 2009/0299291 A1 | 12/2009 | Baid |
| 2010/0010441 A1 | 1/2010 | Belson |
| 2010/0010447 A1 | 1/2010 | Luther et al. |
| 2010/0036331 A1 | 2/2010 | Sen |
| 2010/0056910 A1 | 3/2010 | Yanuma |
| 2010/0087787 A1 | 4/2010 | Woehr et al. |
| 2010/0094310 A1* | 4/2010 | Warring ............ A61M 25/0606 606/108 |
| 2010/0137815 A1 | 6/2010 | Kuracina et al. |
| 2010/0168674 A1 | 7/2010 | Shaw et al. |
| 2010/0204654 A1 | 8/2010 | Mulholland et al. |
| 2010/0204675 A1 | 8/2010 | Woehr et al. |
| 2010/0210934 A1 | 8/2010 | Belson |
| 2010/0238705 A1 | 9/2010 | Kim et al. |
| 2010/0246707 A1 | 9/2010 | Michelitsch |
| 2010/0331732 A1 | 12/2010 | Raulerson et al. |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0125097 A1 | 5/2011 | Shaw et al. |
| 2011/0137252 A1 | 6/2011 | Oster et al. |
| 2011/0196315 A1 | 8/2011 | Chappel |
| 2011/0207157 A1 | 8/2011 | Gautier et al. |
| 2011/0218496 A1 | 9/2011 | Bierman |
| 2011/0251559 A1 | 10/2011 | Tal et al. |
| 2011/0276002 A1 | 11/2011 | Bierman |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2011/0319838 A1 | 12/2011 | Goral et al. |
| 2012/0053523 A1 | 3/2012 | Harding |
| 2012/0078231 A1 | 3/2012 | Hoshinouchi |
| 2012/0101440 A1 | 4/2012 | Kamen et al. |
| 2012/0123332 A1 | 5/2012 | Erskine |
| 2012/0123354 A1 | 5/2012 | Woehr |
| 2012/0157854 A1 | 6/2012 | Kurrus et al. |
| 2012/0179104 A1 | 7/2012 | Woehr et al. |
| 2012/0184896 A1 | 7/2012 | DeLegge et al. |
| 2012/0197200 A1 | 8/2012 | Belson |
| 2012/0220942 A1 | 8/2012 | Hall et al. |
| 2012/0220956 A1 | 8/2012 | Kuracina et al. |
| 2012/0259293 A1 | 10/2012 | Bialecki et al. |
| 2012/0271232 A1 | 10/2012 | Katsurada et al. |
| 2012/0296282 A1 | 11/2012 | Koehler et al. |
| 2012/0316500 A1 | 12/2012 | Bierman et al. |
| 2012/0323181 A1 | 12/2012 | Shaw et al. |
| 2013/0030391 A1 | 1/2013 | Baid |
| 2013/0184645 A1 | 7/2013 | Baid |
| 2013/0204206 A1 | 8/2013 | Morgan et al. |
| 2013/0204226 A1 | 8/2013 | Keyser |
| 2013/0218082 A1 | 8/2013 | Hyer et al. |
| 2013/0304030 A1 | 11/2013 | Gray et al. |
| 2013/0310764 A1 | 11/2013 | Burkholz et al. |
| 2013/0324930 A1 | 12/2013 | Fuchs et al. |
| 2014/0012203 A1 | 1/2014 | Woehr et al. |
| 2014/0031752 A1 | 1/2014 | Blanchard et al. |
| 2014/0039461 A1 | 2/2014 | Anderson et al. |
| 2014/0058329 A1 | 2/2014 | Walker et al. |
| 2014/0058336 A1 | 2/2014 | Burkholz et al. |
| 2014/0058357 A1 | 2/2014 | Keyser et al. |
| 2014/0073928 A1 | 3/2014 | Yamashita et al. |
| 2014/0074034 A1 | 3/2014 | Tanabe et al. |
| 2014/0088509 A1 | 3/2014 | Sonderegger et al. |
| 2014/0094774 A1 | 4/2014 | Blanchard |
| 2014/0094836 A1 | 4/2014 | Feng et al. |
| 2014/0114239 A1 | 4/2014 | Dib et al. |
| 2014/0128775 A1 | 5/2014 | Andreae et al. |
| 2014/0135702 A1 | 5/2014 | Woehr et al. |
| 2014/0135703 A1 | 5/2014 | Yeh et al. |
| 2014/0143999 A1 | 5/2014 | Goral et al. |
| 2014/0180250 A1 | 6/2014 | Belson |
| 2014/0188003 A1 | 7/2014 | Belson |
| 2014/0194853 A1 | 7/2014 | Morgan et al. |
| 2014/0214005 A1 | 7/2014 | Belson |
| 2014/0221977 A1 | 8/2014 | Belson |
| 2014/0236099 A1 | 8/2014 | Nakagami et al. |
| 2014/0249488 A1 | 9/2014 | Woehr |
| 2014/0257359 A1 | 9/2014 | Tegels et al. |
| 2014/0276224 A1 | 9/2014 | Ranganathan et al. |
| 2014/0276434 A1 | 9/2014 | Woehr et al. |
| 2014/0303561 A1 | 10/2014 | Li |
| 2014/0323988 A1 | 10/2014 | Magnani et al. |
| 2014/0336582 A1 | 11/2014 | Tisci et al. |
| 2014/0357983 A1 | 12/2014 | Toomey et al. |
| 2014/0358123 A1 | 12/2014 | Ueda et al. |
| 2014/0364809 A1 | 12/2014 | Isaacson et al. |
| 2014/0371715 A1 | 12/2014 | Farrell et al. |
| 2014/0371720 A1 | 12/2014 | Urmey |
| 2014/0378867 A1 | 12/2014 | Belson |
| 2015/0025467 A1 | 1/2015 | Woehr |
| 2015/0038909 A1 | 2/2015 | Christensen et al. |
| 2015/0038910 A1 | 2/2015 | Harding et al. |
| 2015/0038943 A1 | 2/2015 | Warring et al. |
| 2015/0051584 A1 | 2/2015 | Korkuch et al. |
| 2015/0080801 A1 | 3/2015 | Tanabe et al. |
| 2015/0080810 A1 | 3/2015 | Henderson et al. |
| 2015/0088095 A1 | 3/2015 | Luther et al. |
| 2015/0119806 A1 | 4/2015 | Blanchard et al. |
| 2015/0119852 A1 | 4/2015 | Wexler |
| 2015/0126932 A1 | 5/2015 | Knutsson |
| 2015/0151086 A1 | 6/2015 | Teoh |
| 2015/0151088 A1 | 6/2015 | Lim et al. |
| 2015/0190168 A1 | 7/2015 | Bierman et al. |
| 2015/0190570 A1 | 7/2015 | Teoh |
| 2015/0190617 A1 | 7/2015 | Anderson et al. |
| 2015/0202414 A1 | 7/2015 | Hwang |
| 2015/0224267 A1 | 8/2015 | Farrell et al. |
| 2015/0231364 A1 | 8/2015 | Blanchard et al. |
| 2015/0238705 A1 | 8/2015 | Gravesen et al. |
| 2015/0290431 A1 | 10/2015 | Hall et al. |
| 2015/0306347 A1 | 10/2015 | Yagi |
| 2015/0306356 A1 | 10/2015 | Gill |
| 2015/0328434 A1 | 11/2015 | Gaur |
| 2015/0328438 A1 | 11/2015 | Baid |
| 2015/0335858 A1 | 11/2015 | Woehr et al. |
| 2015/0359473 A1 | 12/2015 | Garrett et al. |
| 2016/0008580 A1 | 1/2016 | Woehr et al. |
| 2016/0015943 A1 | 1/2016 | Belson et al. |
| 2016/0015945 A1 | 1/2016 | Warring et al. |
| 2016/0022312 A1 | 1/2016 | Tang et al. |
| 2016/0022963 A1 | 1/2016 | Belson |
| 2016/0030716 A1 | 2/2016 | Mallin et al. |
| 2016/0045715 A1 | 2/2016 | Galgano et al. |
| 2016/0106959 A1 | 4/2016 | Woehr |
| 2016/0114136 A1 | 4/2016 | Woehr |
| 2016/0114137 A1 | 4/2016 | Woehr et al. |
| 2016/0158503 A1 | 6/2016 | Woehr |
| 2016/0158526 A1 | 6/2016 | Woehr |
| 2016/0175563 A1 | 6/2016 | Woehr et al. |
| 2016/0184557 A1 | 6/2016 | Call et al. |
| 2016/0199575 A1 | 7/2016 | Belley et al. |
| 2016/0206852 A1 | 7/2016 | Morgan et al. |
| 2016/0256667 A1 | 9/2016 | Ribelin et al. |
| 2016/0296729 A1 | 10/2016 | Fuchs et al. |
| 2016/0310704 A1 | 10/2016 | Ng et al. |
| 2016/0331937 A1 | 11/2016 | Teoh |
| 2016/0331938 A1 | 11/2016 | Blanchard et al. |
| 2016/0354580 A1 | 12/2016 | Teoh et al. |
| 2016/0361490 A1 | 12/2016 | Phang et al. |
| 2016/0361519 A1 | 12/2016 | Teoh et al. |
| 2017/0000982 A1 | 1/2017 | Ishida |
| 2017/0035992 A1 | 2/2017 | Harding et al. |
| 2017/0087338 A1 | 3/2017 | Belson |
| 2017/0136217 A1 | 5/2017 | Riesenberger et al. |
| 2017/0203050 A1 | 7/2017 | Bauer et al. |
| 2017/0246429 A1 | 8/2017 | Tan et al. |
| 2017/0259036 A1 | 9/2017 | Belson |
| 2017/0361071 A1 | 12/2017 | Belson |
| 2018/0028780 A1 | 2/2018 | Blanchard et al. |

(56) References Cited

U.S. PATENT DOCUMENTS

| | | |
|---|---|---|
| 2018/0071509 A1 | 3/2018 | Tran et al. |
| 2018/0099123 A1 | 4/2018 | Woehr |
| 2018/0126125 A1 | 5/2018 | Hall et al. |
| 2018/0133437 A1 | 5/2018 | Blanchard |
| 2018/0229003 A1 | 8/2018 | Blanchard et al. |
| 2018/0229004 A1 | 8/2018 | Blanchard et al. |

FOREIGN PATENT DOCUMENTS

| | | |
|---|---|---|
| CN | 1178707 A | 4/1998 |
| CN | 1319023 A | 10/2001 |
| CN | 1523970 A | 8/2004 |
| CN | 1871043 A | 11/2006 |
| CN | 101242868 A | 8/2008 |
| CN | 101417159 A | 4/2009 |
| CN | 101784300 A | 7/2010 |
| CN | 102099075 A | 6/2011 |
| CN | 102939129 A | 2/2013 |
| DE | 20210394 U1 | 9/2002 |
| EP | 0314470 A2 | 5/1989 |
| EP | 417764 A1 | 3/1991 |
| EP | 475857 A1 | 3/1992 |
| EP | 515710 A1 | 12/1992 |
| EP | 567321 A2 | 10/1993 |
| EP | 652020 A2 | 5/1995 |
| EP | 747075 A2 | 12/1996 |
| EP | 750916 A2 | 1/1997 |
| EP | 778043 A1 | 6/1997 |
| EP | 800790 A2 | 10/1997 |
| EP | 832663 A2 | 4/1998 |
| EP | 910988 A1 | 4/1999 |
| EP | 942761 A1 | 9/1999 |
| EP | 1075850 A2 | 2/2001 |
| EP | 1378263 A2 | 1/2004 |
| EP | 1418971 A2 | 5/2004 |
| EP | 1457229 A1 | 9/2004 |
| EP | 1611916 A1 | 1/2006 |
| EP | 1907042 A2 | 4/2008 |
| EP | 2150304 A2 | 2/2010 |
| EP | 2272432 A1 | 1/2011 |
| EP | 2569046 A1 | 3/2013 |
| JP | 2003-159334 A | 6/2003 |
| JP | 2004-130074 A | 4/2004 |
| JP | 2004-223252 A | 8/2004 |
| JP | 2005-137888 A | 6/2005 |
| JP | 2009-500129 A | 1/2009 |
| JP | 2010-088521 A | 4/2010 |
| JP | 2013-529111 | 7/2013 |
| JP | 2018-118079 A | 8/2018 |
| WO | 83/01575 A1 | 5/1983 |
| WO | 1983001575 A1 | 5/1983 |
| WO | 1992013584 A1 | 8/1992 |
| WO | 92/22344 A1 | 12/1992 |
| WO | 1992022344 A1 | 12/1992 |
| WO | 1995011710 A1 | 5/1995 |
| WO | 95/19193 A1 | 7/1995 |
| WO | 1995019193 A1 | 7/1995 |
| WO | 95/23003 A1 | 8/1995 |
| WO | 1995023003 A1 | 8/1995 |
| WO | 96/32981 A1 | 10/1996 |
| WO | 1996032981 A1 | 10/1996 |
| WO | 1996040359 A1 | 12/1996 |
| WO | 97/05912 A2 | 2/1997 |
| WO | 1997005912 A2 | 2/1997 |
| WO | 97/21458 A1 | 6/1997 |
| WO | 1997021458 A1 | 6/1997 |
| WO | 1997045151 A1 | 12/1997 |
| WO | 98/24494 A1 | 6/1998 |
| WO | 1998024494 A1 | 6/1998 |
| WO | 1998030268 A1 | 7/1998 |
| WO | 1998053875 A1 | 12/1998 |
| WO | 1999008742 A1 | 2/1999 |
| WO | 1999026682 A1 | 6/1999 |
| WO | 00/06266 A1 | 2/2000 |
| WO | 00/12160 A1 | 3/2000 |
| WO | 2000012167 A1 | 3/2000 |
| WO | 00/47256 A1 | 8/2000 |
| WO | 2001007103 A1 | 2/2001 |
| WO | 2002041932 A2 | 5/2002 |
| WO | 02/066093 A2 | 8/2002 |
| WO | 03/11381 A1 | 2/2003 |
| WO | 03/43686 A1 | 5/2003 |
| WO | 03/043686 A1 | 5/2003 |
| WO | 03/047675 A2 | 6/2003 |
| WO | 03/47675 A2 | 6/2003 |
| WO | 2004/018031 A2 | 3/2004 |
| WO | 2004106203 A3 | 12/2004 |
| WO | 2005002659 A1 | 1/2005 |
| WO | 2005/074412 A2 | 8/2005 |
| WO | 2005/087306 A1 | 9/2005 |
| WO | 2006062996 A2 | 6/2006 |
| WO | 2007006055 A2 | 1/2007 |
| WO | 2007/032343 A1 | 3/2007 |
| WO | 2007094841 A1 | 8/2007 |
| WO | 2007098355 A1 | 8/2007 |
| WO | 2007098359 A1 | 8/2007 |
| WO | 2008005618 A2 | 1/2008 |
| WO | 2008030999 A2 | 3/2008 |
| WO | 2008/131300 A2 | 10/2008 |
| WO | 2008137956 A2 | 11/2008 |
| WO | 2009/001309 A1 | 12/2008 |
| WO | 2008147600 A1 | 12/2008 |
| WO | 2009031161 A1 | 3/2009 |
| WO | 2009114837 A2 | 9/2009 |
| WO | 2009/124990 A1 | 10/2009 |
| WO | 2010015676 A1 | 2/2010 |
| WO | 2010/048449 A2 | 4/2010 |
| WO | 2010/132608 A2 | 11/2010 |
| WO | 2011036574 A1 | 3/2011 |
| WO | 2011143621 A1 | 11/2011 |
| WO | 2012106266 A1 | 8/2012 |
| WO | 2012154277 A1 | 11/2012 |
| WO | 2012174109 A1 | 12/2012 |
| WO | 2013119557 A1 | 8/2013 |
| WO | 2013126446 A1 | 8/2013 |
| WO | 2013187827 A1 | 12/2013 |
| WO | 2014006403 A1 | 1/2014 |
| WO | 2014029424 A1 | 2/2014 |
| WO | 2014074417 A2 | 5/2014 |
| WO | 2014081942 A1 | 5/2014 |
| WO | 2014/123848 A1 | 8/2014 |
| WO | 2014120741 A1 | 8/2014 |
| WO | 2014133617 A1 | 9/2014 |
| WO | 2014140257 A1 | 9/2014 |
| WO | 2014140265 A1 | 9/2014 |
| WO | 2014/165783 A1 | 10/2014 |
| WO | 2014158908 A1 | 10/2014 |
| WO | 2014182421 A1 | 11/2014 |
| WO | 2014197656 A1 | 12/2014 |
| WO | 2014204593 A1 | 12/2014 |
| WO | 2015017136 A1 | 2/2015 |
| WO | 2015024904 A1 | 2/2015 |
| WO | 2015035393 A1 | 3/2015 |
| WO | 2015058136 A1 | 4/2015 |
| WO | 15108913 A1 | 7/2015 |
| WO | 2015/168655 A2 | 11/2015 |
| WO | 15164912 A1 | 11/2015 |
| WO | 2016/037127 A1 | 3/2016 |
| WO | 2018/049413 A1 | 3/2018 |

OTHER PUBLICATIONS

Access Scientific, The Powerwand® Extended Dwell Catheter Brochure (http://accessscientific.com/media/4Fr-POWERWAND-Brochure.pdf) last accessed Sep. 25, 2015.
BD Angiocath™ Autoguard™ Shielded IV Catheter Brochure, © 2001.
BD Medical Systems, I.V. Catheter Family Brochure (2006).
BD Saf-T-Intima™ Integrated Safety IV Catheter Brochure, © 2001.
Becton Dickinson, Insyte® AutoGuard™ Shielded I.V. Catheter Brochure, 1998.

(56) References Cited

OTHER PUBLICATIONS

CN 201180029526.7 filed Dec. 14, 2012 First Office Action dated Apr. 21, 2014.
CN 2012800008866.6 filed Aug. 14, 2013 Second Office Action dated Aug. 17, 2015.
CN 201280008866.6 filed Aug. 14, 2013 First Office Action dated Dec. 31, 2014.
CN 201280008866.6 filed Aug. 14, 2013 Third Office Action dated Jan. 25, 2016.
CN 201510079782.7 filed Feb. 13, 2015 Office Action dated Dec. 30, 2016.
Cook Medical "Lunderquist Extra-Stiff wire guide" (2012).
Endovascular Today "Coiled Stainless Steel Guidewires" Buyer's Guide pp. 13-20, (2012).
EP 10075422.5 filed Jul. 5, 2008 European search report and written opinion dated Dec. 1, 2010.
EP 12782187.4 filed Sep. 10, 2013 European search report and written opinion dated Aug. 30, 2016.
EP 12782187.4 filed Sep. 10, 2013 European search report and written opinion dated Dec. 17, 2015.
EP 13876666.2 filed Sep. 7, 2015 Extended European Search Report dated Sep. 20, 2016.
European office action dated Apr. 21, 2008 for EP Application No. 06800027.2.
European office action dated Aug. 6, 2012 for EP Application No. 07783404.2.
European office action dated Oct. 5, 2010 for EP Application No. 07783404.2.
European search report and opinion dated Jul. 10, 2009 for EP Application No. 07783404.2.
Hadaway, Lynn C., A Midline Alternative to Central and Peripheral Venous Access, Caring Magazine, May 1990, pp. 45-50.
International search report and written opinion dated Apr. 2, 2012 for PCT/US2012/023192.
International search report and written opinion dated Jun. 1, 2007 for PCT/US2006/026671.
International search report and written opinion dated Oct. 23, 2008 for PCT/US2007/068393.
JP 2013-510353 filed Oct. 31, 2012 First Office Action dated Feb. 19, 2015.
JP 2013-510353 filed Oct. 31, 2012 Office Action dated Dec. 15, 2016.
JP 2013-510353 filed Oct. 31, 2012 Second Office Action dated Jan. 28, 2016.
JP 2016-107046 filed May 30, 2016 Office Action dated Jul. 28, 2016.
Menlo Care, Landmark™ Aquavene® Catheters Brochure, 1992.
Menlo Care, Landmark® Midline Catheter Maintenance and Reference Guide (1993).
Menlo Care, Landmark® Midline Catheters Brochure, 1991.
Menlo Care, Landmark® Venous Access Device Insertion Instructions (1992).
Menlo Care, Publications on Aquavene® Technology, Aug. 1992.
Notice of allowance dated Jan. 29, 2014 for U.S. Appl. No. 12/307,519.
Notice of allowance dated Jun. 10, 2015 for U.S. Appl. No. 11/577,491.
Office action dated Mar. 10, 2011 for U.S. Appl. No. 12/307,519.
Office action dated Mar. 15, 2011 for U.S. Appl. No. 11/577,491.
Office action dated Mar. 27, 2013 for U.S. Appl. No. 13/358,099.
Office action dated Aug. 2, 2010 for U.S. Appl. No. 11/577,491.
Office action dated Aug. 18, 2014 for U.S. Appl. No. 11/577,491.
Office action dated Oct. 25, 2010 for U.S. Appl. No. 12/307,519.
Office action dated Nov. 4, 2013 for U.S. Appl. No. 12/307,519.
Office action dated Mar. 12, 2015 for U.S. Appl. No. 11/577,491.
PCT/US15/28950 filed May 1, 2015 International Search Report and Written Opinion dated Oct. 19, 2015.
PCT/US2008/062954 filed May 7, 2008 International search report and written opinion dated Jan. 16, 2009.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Preliminary Report on Patentability dated Aug. 27, 2013.
PCT/US2012/026618 International Search Report and Written Opinion dated Jun. 25, 2012.
PCT/US2013/073577 filed Dec. 6, 2013 International Search Report and Written Opinion dated Feb. 24, 2014.
PCT/US2014/013557 filed Jan. 29, 2014 International search report and written opinion dated Apr. 14, 2014.
PCT/US2015/048676 filed Sep. 4, 2015 International search report and written opinion dated Dec. 4, 2015.
PCT/US2016/032449 filed May 13, 2016 International Search Report and Written Opinion dated Oct. 5, 2016.
PCT/US2016/032534 filed May 13, 2016 International Search Report and Written Opinion dated Oct. 5, 2016.
PR Newswire, Luther Medical Products, Inc. Receives Approval to Supply Improved Neonatal Product to Japan, Aug. 20, 1998.
Rasor, Julia S, Review of Catheter-related infection rates: comparison of conventional catheter materials with Aquavene®, JVAN vol. 1, No. 3, Spring 1991.
U.S. Appl. No. 12/598,053, filed Apr. 20, 2010 Notice of allowance dated Jan. 16, 2014.
U.S. Appl. No. 12/598,053, filed Apr. 20, 2010 Office action dated Aug. 28, 2013.
U.S. Appl. No. 12/598,053, filed Apr. 20, 2010 Office action dated Dec. 4, 2012.
U.S. Appl. No. 12/598,053, filed Apr. 20, 2010 Office action dated May 8, 2013.
U.S. Appl. No. 12/598,053, filed Apr. 20, 2010 Office action dated Oct. 24, 2013.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.
U.S. Appl. No. 13/405,096, filed Feb. 24, 2012 Advisory Action dated Apr. 18, 2014.
U.S. Appl. No. 13/405,096, filed Feb. 24, 2012 Final Office Action dated Jan. 31, 2014.
U.S. Appl. No. 13/405,096, filed Feb. 24, 2012 Non-Final Office Action dated Aug. 20, 2013.
U.S. Appl. No. 13/405,096, filed Feb. 24, 2012 Non-Final Office Action dated Nov. 18, 2014.
U.S. Appl. No. 13/405,096, filed Feb. 24, 2012 Notice of Allowance dated Mar. 11, 2015.
U.S. Appl. No. 14/044,623, filed Oct. 2, 2013 Notice of Allowance dated Nov. 6, 2014.
U.S. Appl. No. 14/099,050, filed Dec. 6, 2013 Final Office Action dated Jan. 30, 2017.
U.S. Appl. No. 14/099,050, filed Dec. 6, 2013 Non-Final Office Action dated Dec. 22, 2015.
U.S. Appl. No. 14/099,050, filed Dec. 6, 2013 Non-Final Office Action dated Jul. 19, 2016.
U.S. Appl. No. 14/167,149, filed Jan. 29, 2014 Non-Final Office Action dated Oct. 21, 2015.
U.S. Appl. No. 14/167,149, filed Jan. 29, 2014 Notice of Allowance dated Jul. 6, 2016.
U.S. Appl. No. 14/174,071, filed Feb. 6, 2014 Final Office Action dated Dec. 2, 2016.
U.S. Appl. No. 14/174,071, filed Feb. 6, 2014 Non-Final Office Action dated Jul. 29, 2016.
U.S. Appl. No. 14/174,071, filed Feb. 6, 2014 Non-Final Office Action dated Mar. 31, 2016.
U.S. Appl. No. 14/192,541, filed Feb. 27, 2014 Non-Final Office Action dated Jul. 20, 2016.
U.S. Appl. No. 14/192,541, filed Feb. 27, 2014 Notice of Allowance dated Dec. 6, 2016.
U.S. Appl. No. 14/192,541, filed Feb. 27, 2014 Notice of Corrected Allowability dated Mar. 8, 2017.
U.S. Appl. No. 14/250,093, filed Apr. 10, 2014 Final Office Action dated Mar. 9, 2017.

(56) References Cited

OTHER PUBLICATIONS

U.S. Appl. No. 14/250,093, filed Apr. 10, 2014 Non-Final Office Action dated Nov. 16, 2016.
U.S. Appl. No. 14/477,717, filed Sep. 4, 2014, Notice of allowance dated Feb. 17, 2015.
U.S. Appl. No. 14/477,717, filed Sep. 4, 2014, Office action dated Dec. 18, 2014.
U.S. Appl. No. 14/585,800, filed Dec. 30, 2014 Non-Final Office Action dated May 16, 2016.
U.S. Appl. No. 14/585,800, filed Dec. 30, 2014 Non-Final Office Action dated Nov. 29, 2016.
U.S. Appl. No. 14/585,800, filed Dec. 30, 2014 Non-Final Office Action dated Oct. 8, 2015.
U.S. Appl. No. 14/750,658, filed Jun. 25, 2016 Non-Final Office Action dated Mar. 9, 2017.
U.S. Appl. No. 14/866,441, filed Sep. 25, 2015 Advisory Action dated Dec. 22, 2016.
U.S. Appl. No. 14/866,441, filed Sep. 25, 2015 Final Office Action dated Sep. 23, 2016.
U.S. Appl. No. 14/866,441, filed Sep. 25, 2015 Non-Final Office Action dated Mar. 14, 2016.
U.S. Appl. No. 14/866,738, filed Sep. 25, 2015 Final Office Action dated Feb. 24, 2017.
U.S. Appl. No. 14/866,738, filed Sep. 25, 2015 Non-Final Office Action dated Oct. 31, 2016.
Waltimire, B. and Rasor, J.S., Midline catheter: Virtually bloodless insertion technique and needle safety tube minimize potential for transmission of bloodborne disease. Sponsored by national Foundation for Infectious Diseases. 5th National forum on AIDS, Hepatitis, and other blood-borne diseases. Atlanta, GA, Mar. 1992.
CA 2,799,360 filed May 13, 2011 Office Action dated Jun. 7, 2017.
CN 201380073657.4 filed Aug. 21, 2015 Office Action dated Jun. 28, 2017.
CN 201380073657.4 filed Aug. 21, 2015 Office Action dated Mar. 2, 2018.
CN 201480019467.9 filed Sep. 29, 2015 Office Action dated Apr. 6, 2017.
CN 201510079782.7 filed Feb. 13, 2015 Office Action dated Feb. 5, 2018.
CN 201510079782.7 filed Feb. 13, 2015 Office Action dated Sep. 19, 2017.
EP 07783404.2 filed Jan. 19, 2009 Office Action dated Mar. 7, 2018.
EP 11781384.0 filed Sep. 21, 2012 Extended European Search Report dated Oct. 31, 2017.
EP 12782187.4 filed Sep. 10, 2013 Office Action dated Apr. 24, 2018.
EP 15785819.2 filed Dec. 2, 2016 Extended European Search Report dated Dec. 4, 2017.
EP 16797029.2 filed Nov. 21, 2017 Extended European Search Report dated May 3, 2018.
JP 2015-560173 filed Aug. 28, 2015 Office Action dated Aug. 2, 2018.
JP 2015-560173 filed Aug. 28, 2015 Office Action dated Sep. 19, 2017.
JP 2016-107046 filed May 30, 2016 Office Action dated Apr. 26, 2017.
JP 2016-107046 filed May 30, 2016 Office Action dated Nov. 7, 2017.
PCT/CN2017/075370 filed Mar. 1, 2017 International Search Report and Written Opinion dated Nov. 30, 2017.
PCT/US2017/051214 filed Sep. 12, 2017 International Search Report and Written Opinion dated Nov. 13, 2017.
RU 2017141812 filed Nov. 30, 2017 Office Action dated Jan. 31, 2018.
U.S. Appl. No. 14/099,050, filed Dec. 6, 2013 Advisory Action dated Jun. 1, 2017.
U.S. Appl. No. 14/099,050, filed Dec. 6, 2013 Notice of Allowance dated Sep. 14, 2017.
U.S. Appl. No. 14/099,050, filed Dec. 6, 2013 Notice of Panel Decision dated Aug. 1, 2017.
U.S. Appl. No. 14/250,093, filed Apr. 10, 2014 Advisory Action dated May 19, 2017.
U.S. Appl. No. 14/250,093, filed Apr. 10, 2014 Examiner's Answer dated Jun. 20, 2018.
U.S. Appl. No. 14/250,093, filed Apr. 10, 2014 Final Office Action dated Nov. 6, 2017.
U.S. Appl. No. 14/250,093, filed Apr. 10, 2014 Panel Decision dated Jul. 14, 2017.
U.S. Appl. No. 14/585,800, filed Dec. 30, 2014 Final Office Action dated May 11, 2018.
U.S. Appl. No. 14/585,800, filed Dec. 30, 2014 Non-Final Office Action dated Nov. 3, 2017.
U.S. Appl. No. 14/585,800, filed Dec. 30, 2014 Notice of Allowance dated Jul. 3, 2017.
U.S. Appl. No. 14/702,580, filed May 1, 2015 Advisory Action dated Nov. 13, 2017.
U.S. Appl. No. 14/702,580, filed May 1, 2015 Final Office Action dated Sep. 1, 2017.
U.S. Appl. No. 14/702,580, filed May 1, 2015 Non-Final Office Action dated May 3, 2017.
U.S. Appl. No. 14/702,580, filed May 1, 2015 Notice of Allowance dated Dec. 8, 2017.
U.S. Appl. No. 14/750,658, filed Jun. 25, 2016 Notice of Allowance dated Jul. 20, 2017.
U.S. Appl. No. 14/846,387, filed Sep. 4, 2015 Advisory Action dated May 10, 2018.
U.S. Appl. No. 14/846,387, filed Sep. 4, 2015 Final Office Action dated Mar. 22, 2018.
U.S. Appl. No. 14/846,387, filed Sep. 4, 2015 Non-Final Office Action dated Sep. 22, 2017.
U.S. Appl. No. 14/866,441, filed Sep. 25, 2015 Final Office Action dated Jun. 5, 2018.
U.S. Appl. No. 14/866,441, filed Sep. 25, 2015 Non-Final Office Action dated Apr. 7, 2017.
U.S. Appl. No. 14/866,738, filed Sep. 25, 2015 Non-Final Office Action dated Nov. 6, 2017.
U.S. Appl. No. 14/866,738, filed Sep. 25, 2015 Notice of Panel Decision dated Jun. 23, 2017.
U.S. Appl. No. 14/876,735, filed Oct. 6, 2015 Non-Final Office Action dated Mar. 30, 2017.
U.S. Appl. No. 15/154,808, filed May 13, 2016 Final Office Action dated Aug. 16, 2018.
U.S. Appl. No. 15/154,808, filed May 13, 2016 Non-Final Office Action dated Apr. 6, 2018.
U.S. Appl. No. 15/154,808, filed May 13, 2016 Restriction Requirement dated Jan. 3, 2018.
U.S. Appl. No. 15/377,880, filed Dec. 13, 2016 Non-Final Office Action dated May 14, 2018.
U.S. Appl. No. 15/692,915, filed Aug. 31, 2017 Non-Final Office Action dated Jan. 29, 2018.
U.S. Appl. No. 29/536,043, filed Aug. 12, 2015 Final Office Action dated Mar. 26, 2018.
U.S. Appl. No. 29/536,043, filed Aug. 12, 2015 Non-Final Office Action dated Aug. 31, 2017.
U.S. Appl. No. 29/545,436, filed Nov. 12, 2015 Final Office Action dated Mar. 26, 2018.
U.S. Appl. No. 29/545,436, filed Nov. 12, 2015 Non-Final Office Action dated Sep. 12, 2017.
EP 12782187.4 filed Sep. 10, 2013 Office Action dated Nov. 28, 2018.
SG 11201709185X filed Nov. 8, 2017 Office Action dated Oct. 5, 2018.
SG 11201709193S filed Nov. 8, 2017 Office Action dated Oct. 5, 2018.
U.S. Appl. No. 14/846,387, filed Sep. 4, 2015 Notice of Allowance dated Oct. 29, 2018.
U.S. Appl. No. 14/866,441, filed Sep. 25, 2015 Notice of Allowance dated Oct. 17, 2018.
U.S. Appl. No. 15/154,808, filed May 13, 2016 Advisory Action dated Oct. 26, 2018.
U.S. Appl. No. 15/377,880, filed Dec. 13, 2016 Final Office Action dated Oct. 19, 2018.

(56) References Cited

OTHER PUBLICATIONS

U.S. Appl. No. 15/702,537, filed Sep. 12, 2017 Non-Final Office Action dated Nov. 29, 2018.
EP 16797047.4 filed Dec. 6, 2017 Supplemental European Search Report dated Jan. 9, 2019.
JP 2016-563441 filed Oct. 19, 2016 Office Action dated Jan. 25, 2019.
U.S. Appl. No. 14/585,800, filed Dec. 30, 2014 Notice of Allowance dated Feb. 25, 2019.
U.S. Appl. No. 15/154,384, filed May 13, 2016 Restriction Requirment dated Jan. 25, 2019.
U.S. Appl. No. 15/702,537, filed Sep. 12, 2017 Final Office Action dated Mar. 8, 2019.
JP 2018-039302 filed Mar. 6, 2018 Office Action dated Feb. 20, 2019.
U.S. Appl. No. 15/154,808, filed May 13, 2016 Notice of Allowance dated Apr. 16, 2019.

* cited by examiner

INTRAVENOUS CATHETER AND INSERTION DEVICE WITH REDUCED BLOOD SPATTER

CROSS-REFERENCE TO RELATED APPLICATIONS

This application is a continuation of U.S. patent application Ser. No. 14/192,541, filed Feb. 27, 2014, now U.S. Pat. No. 9,616,201, which is a continuation of U.S. patent application Ser. No. 13/358,099, filed Jan. 25, 2012, now U.S. Pat. No. 8,690,833, which claims the benefit of U.S. Provisional Patent Application No. 61/438,197, filed Jan. 31, 2011, each of which is incorporated herein by reference in its entirety.

BACKGROUND OF THE INVENTION

1. Field of the Invention

The present invention relates to devices and methods for insertion and placement of an access catheter into a vein or artery of a patient over a guidewire.

Safe placement of an access catheter into the patient's vein or artery is particularly difficult in the case of small, tortuous, collapsed, fragile, and/or difficult to locate vessels. The risk of accidental punctures and/or contamination by the needle after placement of an intravenous catheter is a particular problem. It is therefore of interest to provide devices and methods which protect medical personnel from potential exposure to blood from the movement of the retracting guidewire.

Of particular interest to the present invention, access catheters are often pre-packaged with both a needle and a guidewire where the needle is coaxially received over the guidewire and the catheter is coaxially received over the needle. The needle extends just beyond the distal tip of the catheter so that the assembly of the needle and catheter can be introduced into the vein or other vessel. As soon as entry into the vein is detected, typically by observing flashback, the guidewire can be advanced into the venous lumen, the catheter advanced over the guidewire, and both the needle and guidewire then removed from the catheter, leaving the catheter available for attachment to sources of fluids, drugs or other intravenous materials.

Removal of the needle and guidewire can be problematic as they have a tendency to carry patient blood and risk the treating personnel to exposure. This can be a particular problem in the case of guidewires having a helical or other shaped tip, such as those described in at least some of the published U.S. patent applications listed below.

For these reasons, it would be desirable to provide systems and methods for use with intravenous and other vascular access catheters to reduce the risk of blood loss and spattering where guidewires and/or needles are withdrawn from the catheter after placement. It would be particularly desirable if such methods and devices were compatible with venous catheters having automatic needle and guidewire retraction mechanisms, as described in the patent publications listed below. At least some of these objectives will be met by the invention as described herein.

2. Background Art

The subject matter of the present invention is related to the following U.S. patent publications, the disclosures of which are hereby incorporated by reference in their entirety. Each of the various embodiments of an intravenous catheter insertion device described in these patent applications can be combined with the intravenous catheter of the present invention to create an intravenous catheter system.

U.S. Pat. No. 8,721,546, titled, "Intravenous catheter insertion and blood sample devices and method of use." U.S. Pat. No. 8,728,035, titled, "Intravenous catheter insertion device and method of use." U.S. Pat. No. 9,162,037, titled, "Intravenous catheter insertion device and method of use." Also of interest are the following U.S. patents that describe catheters having sidearm connectors: U.S. Pat. Nos. 5,704,914; 5,154,703; 5,084,023; 4,585,440; 4,509,534; and 4,177,809.

BRIEF SUMMARY OF THE INVENTION

The present invention provides venous and other vascular access catheters which are adapted to reduce the loss and spattering of blood upon withdrawal of needles and guidewires used to introduce the catheters. In particular, the present invention provides a catheter insertion device comprising an access catheter, a needle, a safety guidewire, and an actuator mechanism for selectively advancing the safety guidewire through the needle and selectively withdrawing both the needle and the safety guidewire from the catheter at desired points in the catheter insertion protocol. The present invention provides a chamber and a septum or other membrane as a "wiping" element on a proximal hub, housing, or other component of the access catheter. The chamber is preferably disposed at a proximal end of a hub having an interior chamber spaced apart from a proximal end of the catheter. A septum is preferably disposed on a proximal side of the chamber to wipe residual blood from the guidewire as the guidewire is withdrawn by the actuator. An insertion tool for the needle and/or guidewire is removably attached to the hub adjacent the septum so that the needle and guidewire may be advanced through the septum and into the catheter for selective advancement in order to permit introduction of the catheter into an artery or vein in a generally conventional manner. The actuator is further adapted to withdraw the needle and guidewire, typically under the force of a spring or other biasing element which rapidly withdraws the needle and catheter into and through the interior of the hub. Usually, the guidewire will be a "safety" guidewire having a helical or other preformed atraumatic shape at its distal end which is assumed when the safety guidewire exists from a distal tip of the needle in order to reduce the risk of damaging the vessel as the guidewire is advanced. As the guidewire is withdrawn, the safety tip will be straightened as it passes through the needle lumen and will resume the helical or other configuration within the interior of the hub, thus being able to shed blood which it may have picked up while in the artery or vein into the hub rather than into the surrounding tissue or housing. The guidewire can then be further withdrawn through the septum in order to remove any remaining blood before it is drawn back into the actuator for safe disposal. A side port, typically with a side tube, is provided on the hub in order to introduce desired fluids in order to accommodate the septum or other wiping element which is present on the proximal end of the hub.

BRIEF DESCRIPTION OF DRAWINGS

FIG. 10 is a proximal end view of the guidewire, and

FIG. 11 is a side view of the guidewire.

DETAILED DESCRIPTION OF THE INVENTION

Figure 1:
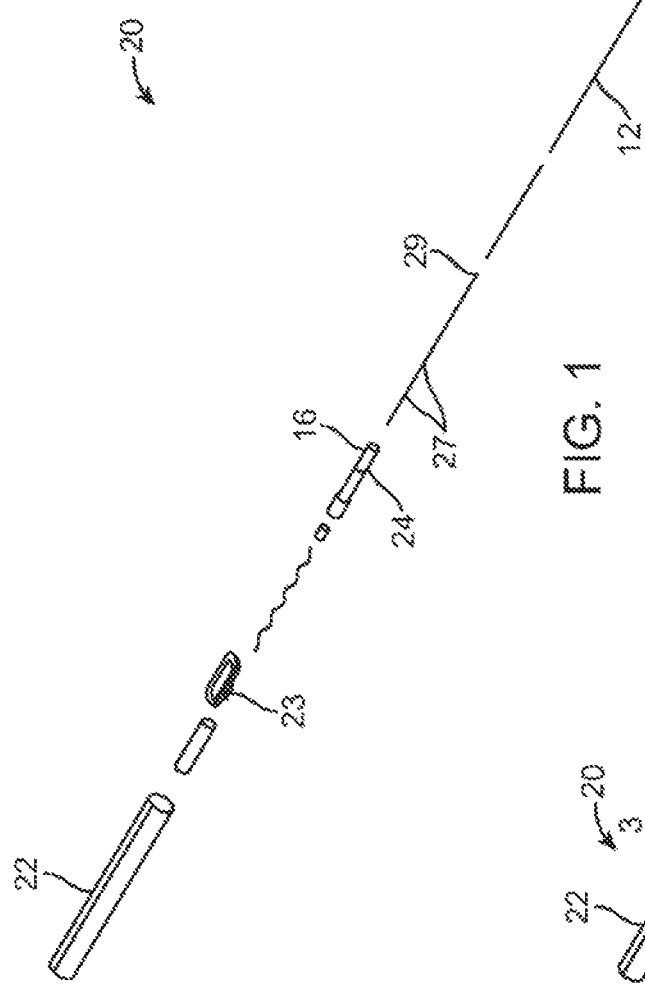
FIG. 1 shows an exploded view of an intravenous catheter and insertion device according to the present invention.
Figure 2:
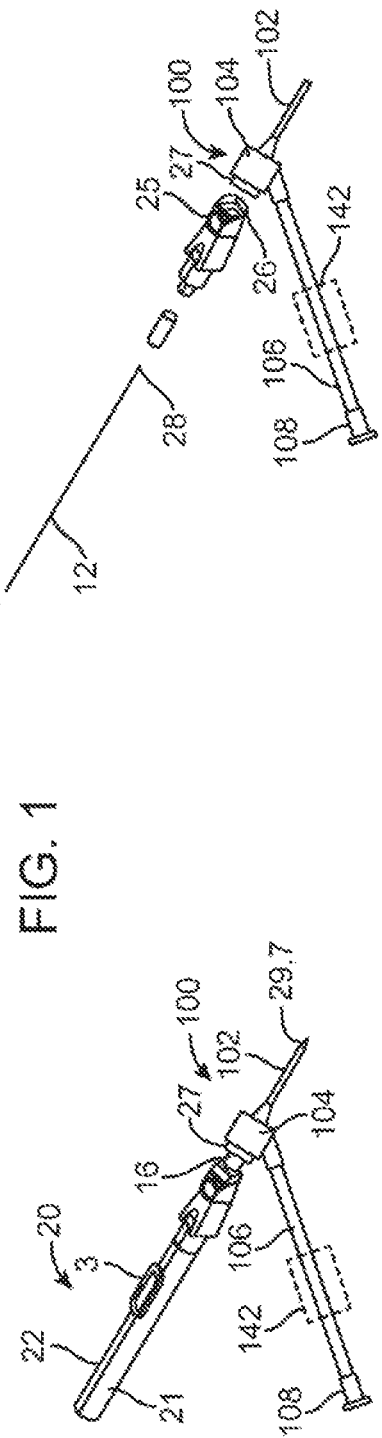
FIG. 2 shows an assembly drawing of the intravenous catheter and insertion device in an undeployed state, ready for use.

FIG. 1 shows an exploded view of one embodiment of an intravenous catheter 100 and insertion device 20 according to the present invention. FIG. 2 shows an assembly drawing of the intravenous catheter 100 and insertion device 20 in an undeployed state, ready for use. Additional intravenous catheter insertion devices that can be used in the present invention are described in detail in the following patents: U.S. Pat. No. 8,721,546, U.S. Pat. No. 8,728,035 and U.S. Pat. No. 9,162,037, which have been incorporated by reference.

The intravenous catheter insertion device 20 has a housing 21, which includes a proximal housing 1 that is adhesively joined or otherwise connected to a distal housing 11. In the example shown, the proximal housing 1 is in the form of an elongated hollow cylinder. The distal housing 11 is optionally formed in an ergonomic handle shape designed to be held by the thumb and forefinger of a user. Other shapes are also possible. The housing 21 has an elongated slot 22 that extends from the proximal housing 1 to the distal housing 11 approximately parallel with a longitudinal axis of the housing 21. A wire advance slider 3 slides in a longitudinal direction along an exterior of the proximal housing 1 and the distal housing 11 and has a tongue 23 that extends through the slot 22 into the interior of the housing 21. A needle carrier 6 is slidable within the interior of the housing 21 and is positioned distal to the tongue 23 of the wire advance slider 3. The distal end of the needle carrier 6 includes a luer slip fitting 16 or the like. There is a notch 24 in the needle carrier 6 just proximal to the luer slip fitting 16. A button 25 is located on one side of the distal housing 11, which has a tab 26 that is configured to engage the notch 24 in the needle carrier 6 when the needle carrier 6 is in its most distal position. A cylindrical guidewire stop 2 is adhesively bonded into the proximal end of the proximal housing 1.

Figure 9:
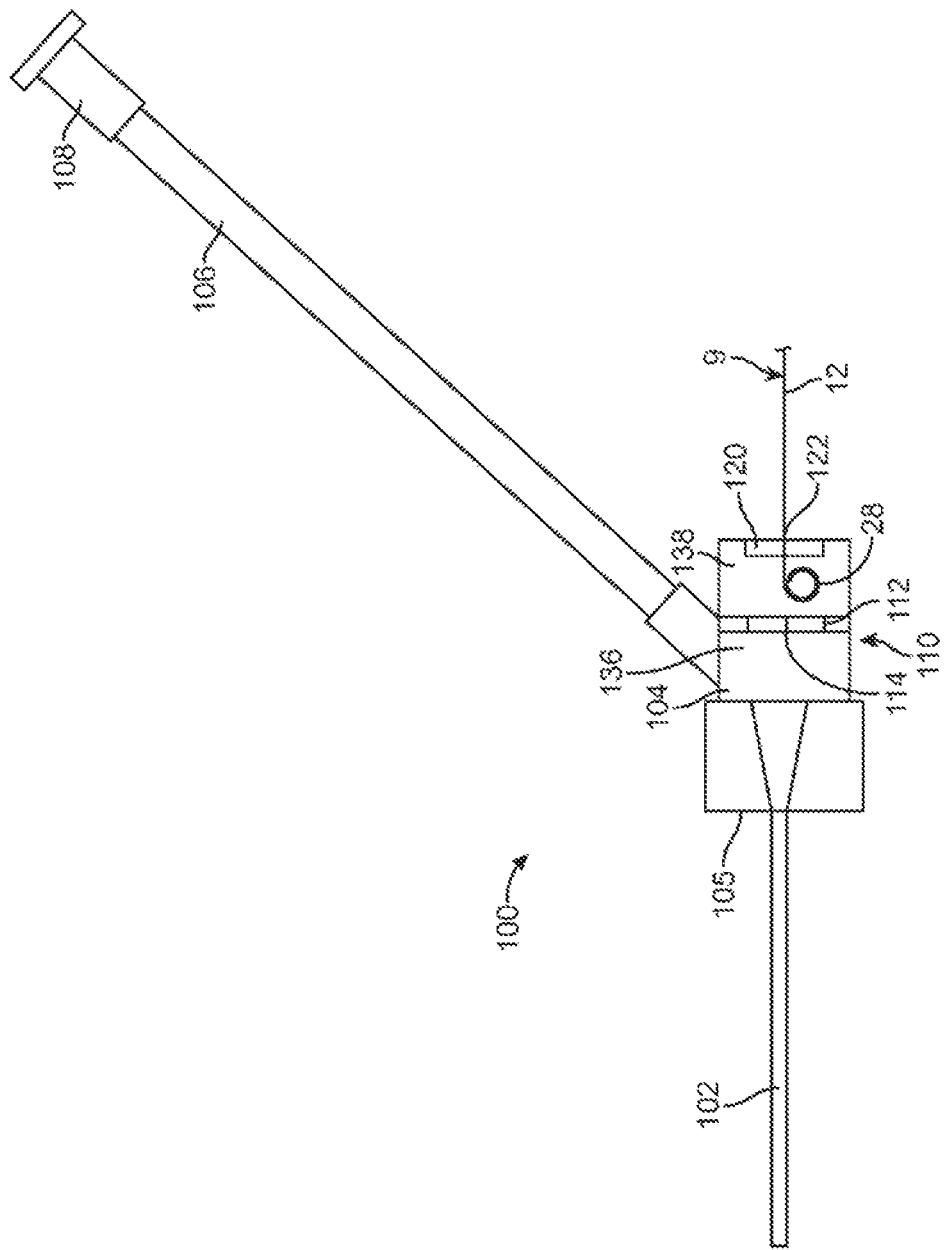
FIG. 9 is an enlarged view of another embodiment of an intravenous catheter according to the present invention.

A tubular stainless steel hypodermic needle 7 with a sharpened, beveled distal end 29 is bonded with adhesive 13 or otherwise attached to the distal end of the needle carrier 6. Preferably, the needle 7 has one or more slots 27 cut into the sides of it connecting to the needle lumen for the passage of blood. A guidewire 9 is bonded with adhesive 14 or otherwise attached to the tongue 23 of the wire advance slider 3. The guidewire 9 is preferably made of a highly resilient material, such as a superelastic Nickel-Titanium alloy wire approximately 0.003-0.012 inches in diameter and most preferably approximately 0.004 inches in diameter. The guidewire 9 may be uniform in diameter or it may be made stepped or tapered in diameter, for example by grinding. For example, a 0.008 inch diameter wire can be centerless ground to create a 0.004 inch diameter distal portion with a short tapered transition. Optionally, a proximal portion of the guidewire 9 may be supported with a support tube 8 made from stainless steel or Nickel-Titanium alloy hypodermic tubing or a molded or extruded polymer tube. Another option for constructing the guidewire 9 would be to join a short distal portion of a highly resilient material, such as a superelastic Nickel-Titanium alloy wire, to a larger diameter, solid or tubular proximal portion, for example by welding, swaging, crimping and/or adhesive bonding. As best seen in FIG. 9, the distal end of the guidewire 9 is preformed into a tightly wound spiral 28 with an outer diameter smaller than the internal diameter of the target vessel into which it will be inserted. The spiral tip 28 acts as a safety bumper on the guidewire 9 to avoid puncturing or damaging the inside of target vessels. The coiled guidewire tip 28 is particularly useful in protecting fragile or delicate veins. Due to the extreme flexibility of the Nickel-Titanium alloy wire, the spiral distal curve 28 can straighten out when the guidewire 9 is withdrawn into the needle 7 and completely recover into the spiral configuration without plastic deformation when the guidewire 9 is advanced out of the needle 7. In the example shown, the distal end of the guidewire 9 has a first, small diameter coil of approximately 0.167 inches in diameter for approximately 0.75 revolutions and a second, larger diameter coil of approximately 0.175 inches in diameter for approximately 1 revolution. The first and second coils are preferably approximately coplanar with one another and preferably approximately coplanar with the straight proximal portion 12 of the guidewire 9 also. Other configurations of the guidewire 9 may include: multi-planar, single coil, full radius on the end, and/or a balled end with a diameter less than the diameter of the needle.

The guidewire 9 is positioned to move coaxially through the lumen of the needle 7. Optionally, a flexible tether 4 connects from the tongue 23 of the wire advance slider 3 to the proximal end of the needle carrier 6. Optionally, a needle carrier cap 5 may be provided to facilitate adhesively attaching the tether 4 to the proximal end of the needle carrier 6. The length of the tether 4 prevents the guidewire 9 from being withdrawn too far proximally with respect to the needle 7 because the small-diameter distal coil 28 would be difficult to reinsert into the proximal end of the needle 7 if it were to be completely withdrawn from the needle lumen. In another option, instead of using a tether, a plastic protrusion or another physical structure, such as a gate, can act as a detent to block the guidewire 9 from withdrawing beyond the desired point. Optionally, the detent may be configured so that it can be overrun when a forceful retraction occurs, such as the one that is initiated by the spring 10, thus allowing complete retraction of the guidewire 9. In another option, the housing 21 may be configured such that the guidewire 9 or the structure that is connected to the guidewire 9 will hit a positive stop, such as the guidewire stop 2 or the proximal end of the housing 21, before the guidewire 9 gets to a position too proximal relative to the needle 6.

The proximal housing 1, distal housing 11, wire advance slider 3, button 25, needle carrier 6, guidewire stop 2 and needle carrier cap 5 may be formed from any material suited for use in medical applications. For example, some or all of these parts may be molded and/or machined from a rigid, transparent medical grade plastic, such as acrylic or polycarbonate.

A compression spring 10 or similar biasing member is positioned between the needle carrier 6 and the distal end of the housing 21 to urge the needle carrier 6 in a proximal direction. The force of the spring 10 is resisted by the tab 26 of the button 25, which engages the notch 24 in the needle carrier 6 when the needle carrier 6 is in its most distal position. It should be noted that in FIG. 1 the spring 10 is shown in a compressed condition as it would be in the assembled intravenous catheter insertion device 20 in an undeployed condition.

Figure 6:
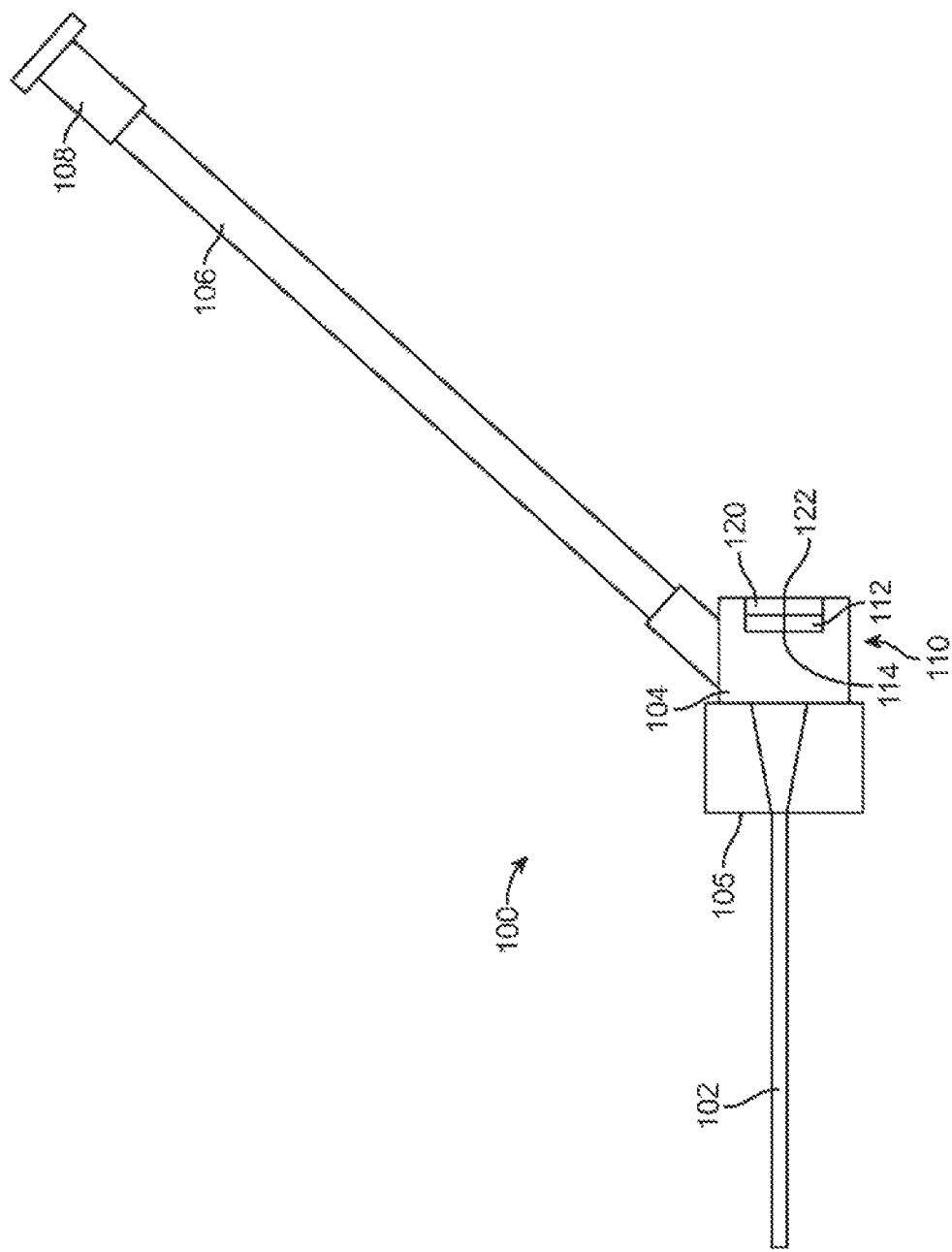
FIG. 6 is an enlarged view of the intravenous catheter of FIG. 3.

The intravenous catheter 100, which is shown in an enlarged view in FIG. 6, has a catheter tube 102 with an inner lumen that fits coaxially around the needle 7 of the insertion device 20. The catheter tube 102 is preferably extruded of a flexible medical grade polymer having a low coefficient of friction, for example PTFE, polypropylene or polyethylene. Preferably, the intravenous catheter tube 102 has a close fit with the needle 7 and a tapered distal end to minimize any step between the needle 7 and the catheter tube 102 as they are inserted through the wall of a vein.

The proximal end of the catheter tube 102 is connected to a proximal fitting 104 that connects to the distal end of a flexible sidearm tube 106, which extends laterally from the side of the proximal fitting 104. Preferably, the proximal fitting 104 is molded of a clear polymer so that blood flashback from the needle 7 can be observed in the proximal fitting 104. A luer fitting 108 or the like is attached to the proximal end of the sidearm tube 106. A fluid flow path is formed from the luer fitting 108 through the sidearm tube 106 to the proximal fitting 104 and the catheter tube 102. Preferably, the fluid flow path is free of obstructions, sudden changes of diameter or dead spaces that would interfere with fluid flow or be a nidus for thrombus formation. Optionally, the intravenous catheter 100 may include wings 105, which facilitate taping the intravenous catheter 100 to the patient's skin after insertion. The wings 105 may be rigid or flexible and, optionally, may be molded integrally with the proximal fitting 104.

The hemostasis valve 110 is preferably configured as an elastomeric membrane 112 with a small hole 114 at the center of the elastomeric membrane 112. The hole 114 forms a sliding seal around the needle 7 of the insertion device 20. Alternatively, the elastomeric membrane 112 may be intact and the needle 7 will form a hole 114 as it is inserted through the membrane 112. The elastomeric membrane 112 can be made of latex, silicone, polyurethane or another medical grade elastomer. Optionally, a small amount of medical grade lubricant, such as silicone oil, may be used to reduce the friction of the needle 7 passing through the hemostasis valve 110. Other configurations of hemostasis valves known in the industry, such as those having different configurations of membranes, holes, slits or duckbill valves, may also be used. Optionally, more than one or a combination of different hemostasis valves 110 may be used.

Optionally, located proximal to the hemostasis valve 110 is a wiping element 120. The wiping element 120 is adapted to remove blood from the surface of the guidewire 9 and needle 7 as they are withdrawn from the intravenous catheter 100. The wiping element 120 may be made of an absorbent or superabsorbent material to absorb blood from the surface of the needle 7 and guidewire 9. Examples of suitable materials include, but are not limited to, cotton wool, gauze, felt, natural or artificial sponge, open-cell foam, etc. Alternatively, the wiping element 120 may be configured as an elastomeric membrane that acts like a squeegee to remove blood from the surface of the guidewire 9. The elastomeric membrane will preferably be sufficiently elastic to adapt to the larger diameter of the needle 7 and then to the smaller diameter of the guidewire 9 when the needle 6 has been withdrawn. Preferably, the wiping element 120 is made with a hole or slit 122 in the center that is aligned with the hole 114 in the hemostasis valve 110. Alternatively, the wiping element 120 may be intact and the needle 7 will form a hole 122 as it is inserted through the wiping element 120.

Optionally, there may be a luer fitting 27 or the like on the proximal fitting 104 of the intravenous catheter 100 that fits onto a luer slip fitting 16 on the distal end of the needle carrier 6 with a slight interference fit to hold the intravenous catheter 100 in place, as shown in FIGS. 1 and 2. Alternative configurations of the device may use a luer lock or other locking mechanism to temporarily attach the intravenous catheter 100 to the insertion device 20. Alternatively, the friction of the needle 7 passing though the hemostasis valve 110 and wiping element 120 may be sufficient to hold the intravenous catheter 100 onto the insertion device 20.

An optional feature of the intravenous catheter 100 in any of the embodiments described herein is a means 142 for selectively blocking or occluding fluid flow through the flexible sidearm tube 106. This can be in the form of a tubing clamp or stopcock located on the flexible sidearm tube 106 or on the luer fitting 108, as shown in FIGS. 1 and 2. Alternatively, a separate stopcock can be connected to the luer fitting 108 for selectively blocking fluid flow.

Figure 3:
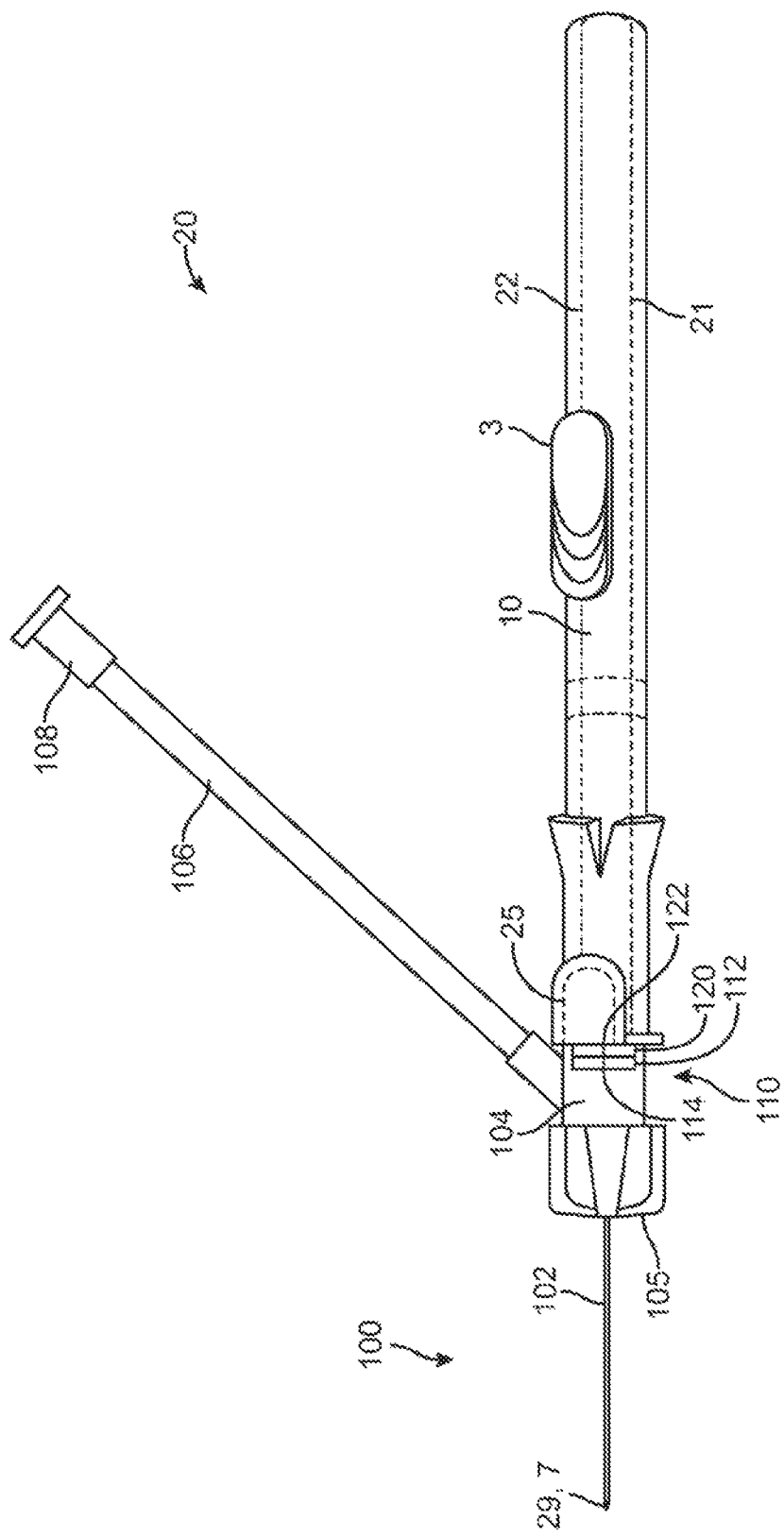
FIG. 3 shows an intravenous catheter and insertion device in an undeployed state, ready for use.
Figure 4:
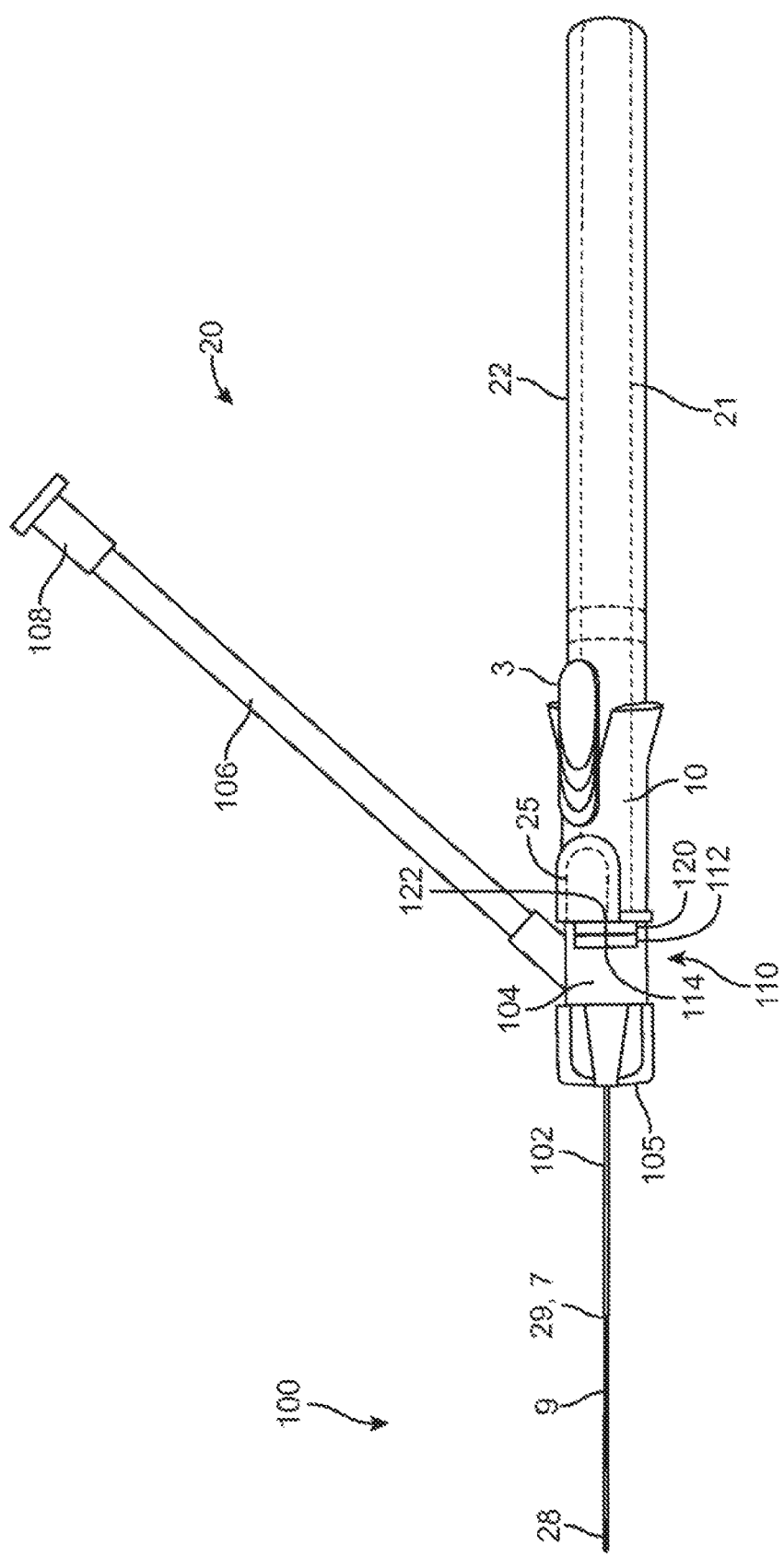
FIG. 4 shows the intravenous catheter and insertion device of FIG. 3 with the guidewire advanced.
Figure 5:
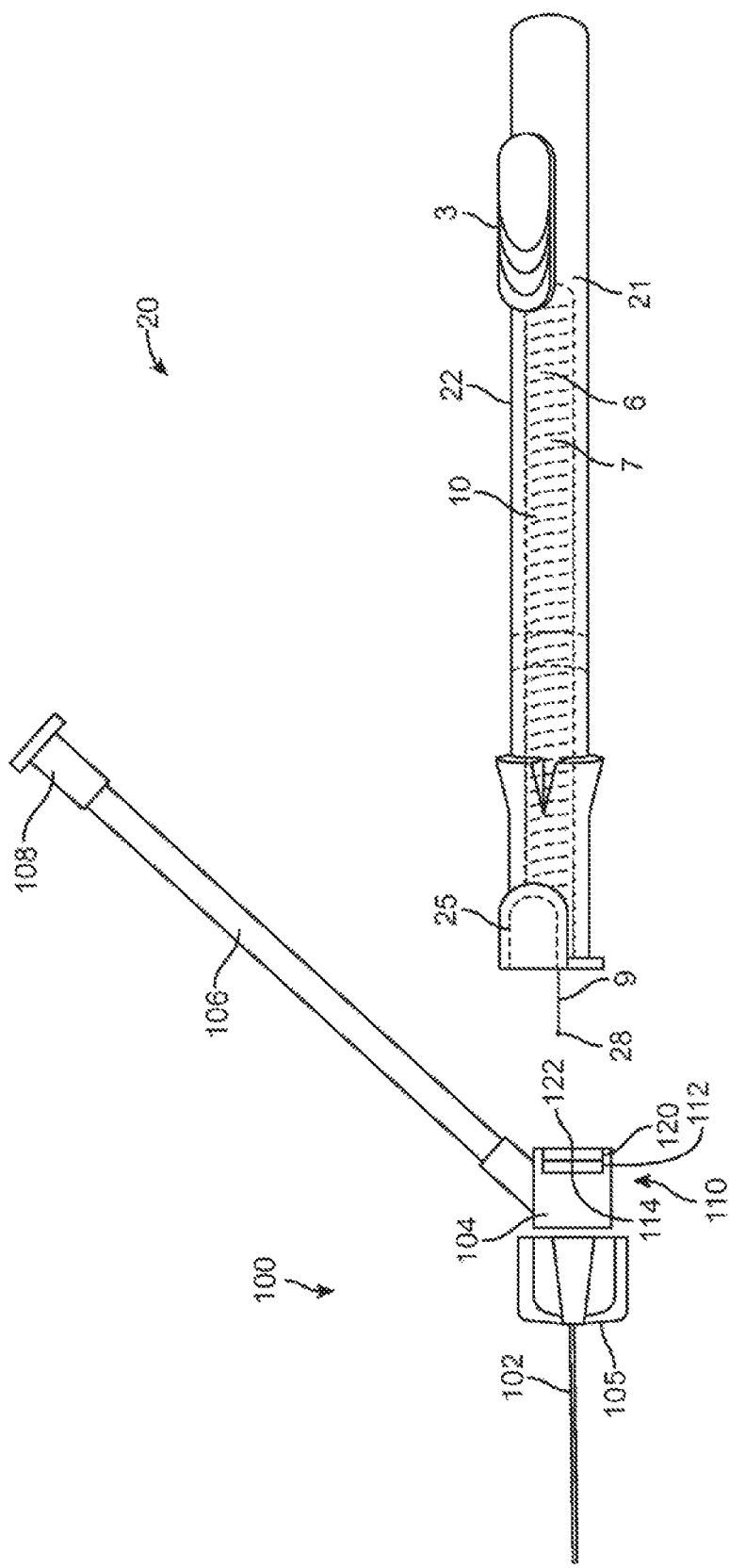
FIG. 5 shows the intravenous catheter and insertion device of FIG. 3 with the guidewire and needle retracted.

FIGS. 3-5 illustrate steps in a method of inserting an intravenous catheter 100 using an intravenous catheter insertion device 20, such as those described above in connection with FIGS. 1, 2 and 6. The intravenous catheter 100 and insertion device 20 are provided as a single-use, non-reusable device supplied to the physician or other medical practitioner sterile in a ready-to-use, undeployed condition, as shown in FIG. 3. In another option, the device can be stored with the distal spiral portion 28 of the guidewire 9 advanced distally from the tip of the needle 7 so that it is not straightened during storage. In this case, the operator will fully retract the guidewire 9 into the needle 7 before use. In use, the operator uses the housing 21 as a handle to manipulate the intravenous catheter 100 and insertion device 20. With the device in the undeployed condition, the needle 7 is used to puncture a vein. When venous blood is observed in the proximal fitting 104, the operator knows that the distal tip of the needle 7, together with the distal part of the catheter tubing 102, is in the lumen of the vein. The operator can then advance the slider 3 in the distal direction to extend the guidewire 9 out of the needle 7 into the lumen of the vein, as shown in FIG. 4. The distal portion of the guidewire 9 assumes its spiral configuration 28 to act as a safety bumper to prevent accidental puncture of the far wall of the vein or other damage to the vein and also to enable passage along obstructions such as valves or curves. With the guidewire 9 thus deployed, the operator can safely continue advancing the intravenous catheter 100 until it is inserted far enough into the vein, then the operator pushes the button 25, which disengages the tab 26 from the notch 24 in the needle carrier 6. The spring 10 urges the needle carrier 6 and the slider 3 in the proximal direction, thus simultaneously withdrawing the needle 7 and the guidewire 9 into the housing 21, leaving only the intravenous catheter 100 in the lumen of the vein. FIG. 5 shows the insertion device 20 with the needle 7 and the guidewire 9 withdrawn into the housing 21. Preferably, the coil 28 on the distal tip of the guidewire 9 is visible when the insertion device 20 is in the deployed position, as shown in FIG. 5. This allows the operator to verify that the guidewire 9 is intact and that only the intravenous catheter 100 has been left in the patient's vein.

While it is desirable for the insertion device 20 to withdraw the needle 7 and the guidewire 9 simultaneously, the actuator mechanism could also be modified to withdraw the needle 7 and the guidewire 9 sequentially. For example, the actuator mechanism could withdraw the needle 7 first and then, after a slight delay, withdraw the guidewire 9. Alternatively, the actuator mechanism could be modified to require two separate motions of one actuator member or selective movements of two separate actuator members to withdraw the needle 7 and the guidewire 9 selectively. As another alternative, the spring 10 may be omitted from the actuator mechanism, thus allowing the needle 7 and the guidewire 9 to be withdrawn manually using the slider 3. Once the intravenous catheter 100 has been inserted into the patient's vein, the slider 3 is moved proximally along the slot 22 to withdraw the needle 7 and the guidewire 9 into the housing 21.

Figure 7:
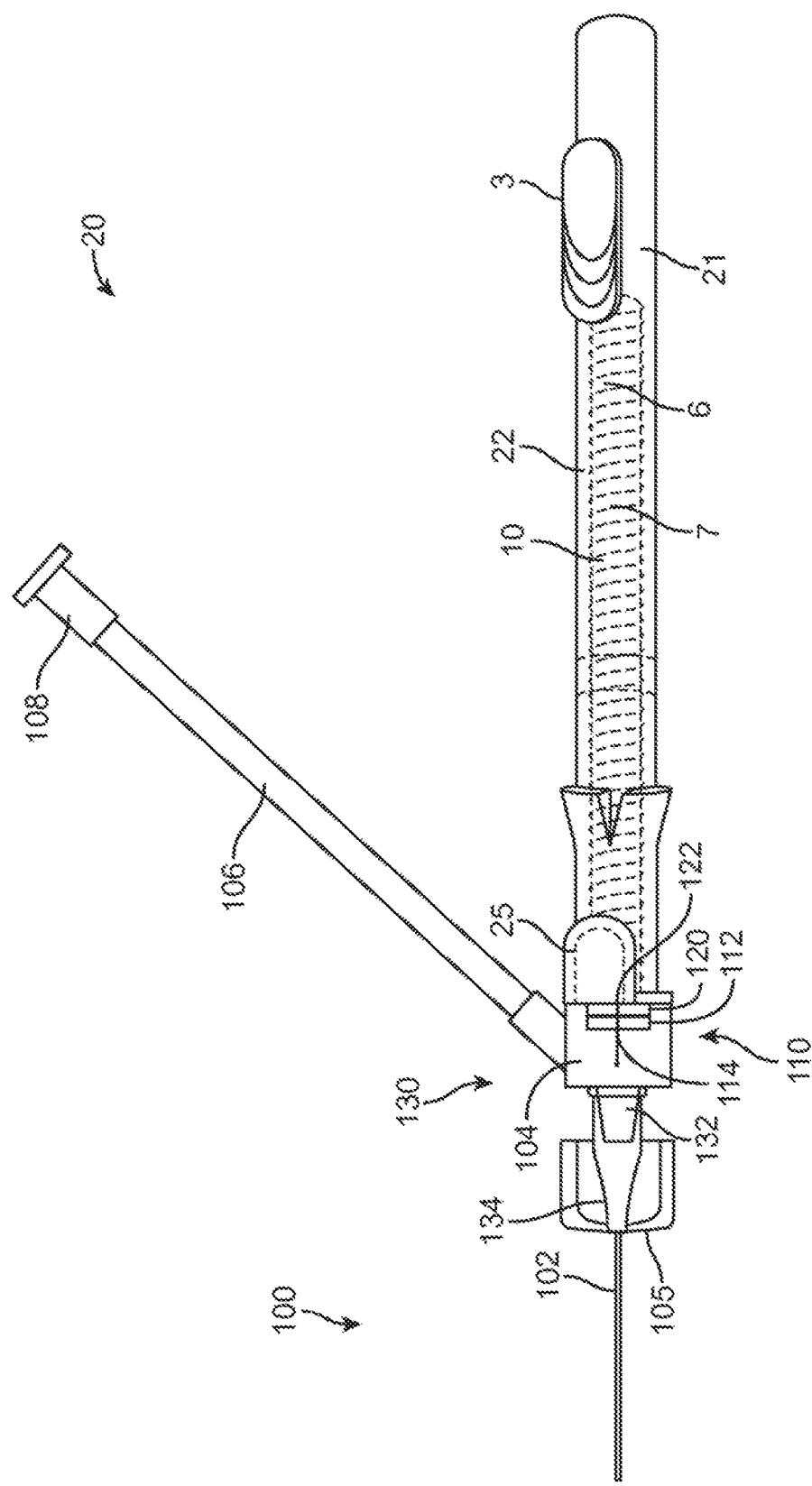
FIG. 7 shows an embodiment of the intravenous catheter and insertion device with a separate sidearm adapter.
Figure 8:
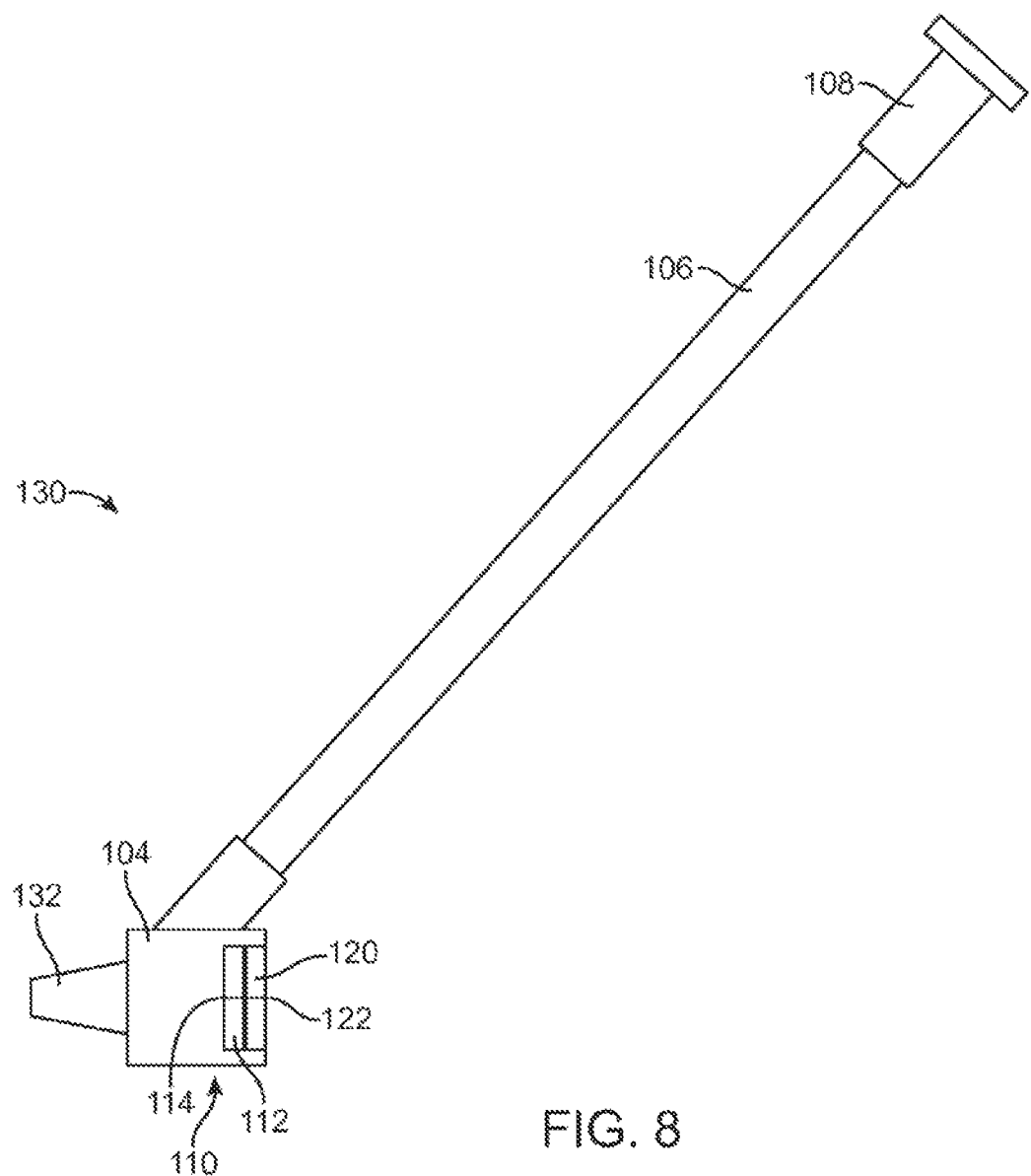
FIG. 8 is an enlarged view of the sidearm adapter of FIG. 7.

FIG. 7 shows an embodiment of the intravenous catheter 100 and insertion device 20 with a separate sidearm adapter 130. FIG. 8 is an enlarged view of the sidearm adapter 130 of FIG. 7. The structure of the intravenous catheter 100 is similar to that described above in connection with FIG. 6, except that the proximal fitting 104 has a male luer connector 132 on its distal end that interlocks with a female luer connector 134 on the proximal end of the catheter tube 102.

FIG. 9 is an enlarged view of another embodiment of an intravenous catheter 100 according to the present invention. The proximal fitting 104 and the sidearm 106 may be integral to the intravenous catheter 100, as shown in FIG. 9, or they may be part of a separate sidearm adapter, similar to that shown in FIGS. 7 and 8. In this embodiment, the proximal fitting 104 has a first chamber 136 in fluid connection with the catheter tube 102 and a second chamber 138 separated from the first chamber 136 by the hemostasis valve 110. Optionally, a wiping element 120 for removing blood from the guidewire 9 is located on the proximal side of the second chamber 138. Preferably, the second chamber 138 is sized to allow the coiled tip 128 of the guidewire 9 to resume its coiled configuration after it is withdrawn through the hemostasis valve 110. Any dripping or spattering of blood from the guidewire 9 will occur in the second chamber 138. The optional wiping element 120 will help to remove any remaining blood from the guidewire 9 as it is withdrawn from the second chamber 138.

Figure 11:
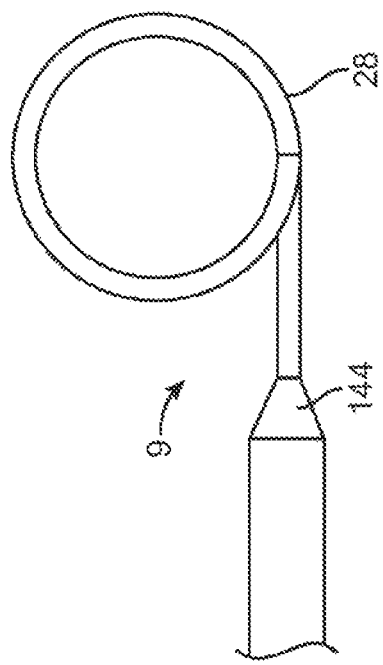
FIGS. 10 and 11 illustrate another embodiment of a guidewire for use with the intravenous catheter and insertion device.
Figure 10:
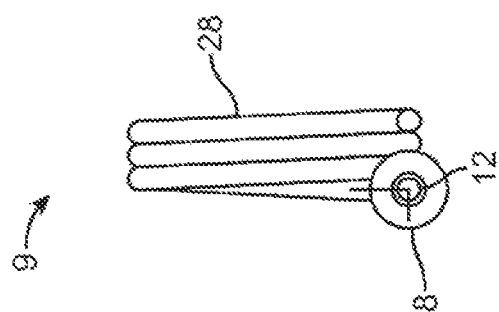

FIGS. 10 and 11 illustrate another preferred embodiment of a guidewire 9 for use with the intravenous catheter 100 and insertion device 20 of the present invention. FIG. 10 is a proximal end view of the guidewire 9, and FIG. 11 is a side view of the guidewire 9. The guidewire 9 is preferably made of a highly resilient material, such as a superelastic Nickel-Titanium alloy wire with a uniform diameter of approximately 0.003-0.012 inches and most preferably approximately 0.004 inches. The distal end of the guidewire 9 is preformed into a tightly wound spiral 28 with an outer diameter smaller than the internal diameter of the target vessel into which it will be inserted. Due to the extreme flexibility of the Nickel-Titanium alloy wire, the spiral distal curve 28 can straighten out when the guidewire 9 is withdrawn into the needle 7 and completely recover into the spiral configuration without plastic deformation when the guidewire 9 is advanced out of the needle 7. In the example shown, the spiral distal curve 28 of the guidewire 9 is in the form of a helix with approximately three coils or rotations of substantially uniform diameter. In a particularly preferred embodiment, the helical coils of the spiral distal curve 28 have an outer diameter of approximately 0.052 inches (approximately 1.3 mm). Alternatively, the spiral distal curve 28 may be in the form of a conical helix with coils that diminish or increase in diameter. In the example shown, the helical coils of the spiral distal curve 28 have a central axis that is perpendicular to and offset from an axis defined by the proximal portion 12 of the guidewire 9. In other embodiments, the central axis of the spiral distal curve 28 may be skewed from the axis of the proximal portion 12 of the guidewire 9. Other possible configurations of the spiral distal curve 28 of the guidewire 9 are described in patents U.S. Pat. No. 8,721,546, U.S. Pat. No. 8,728,035, and U.S. Pat. No. 9,162,037, which have been incorporated by reference.

The proximal portion 12 of the guidewire 9 is preferably supported with a support tube 8 made from stainless steel or Nickel-Titanium alloy hypodermic tubing or, alternatively, a molded or extruded tube made of a polymer, such as, but not limited to, FEP, PEEK or HDPE. The support tube 8 will preferably have an inner diameter sufficient for the proximal portion 12 of the guidewire 9 to be inserted through it, for example 0.006 inches inner diameter to accommodate a 0.004 inch diameter guidewire 9. The support tube 8 will preferably have an outer diameter of approximately 0.012-0.016 inches and most preferably approximately 0.014 inches. Optionally, the support tube 8 may be adhesively bonded or otherwise attached to the proximal portion 12 of the guidewire 9 with the distal end of the support tube 8 positioned a short distance proximal to the spiral distal curve 28. The support tube 8 may have a tapered distal end 144, which may be formed by a molding process or by applying a filet of adhesive or other material during assembly.

Figure 12:
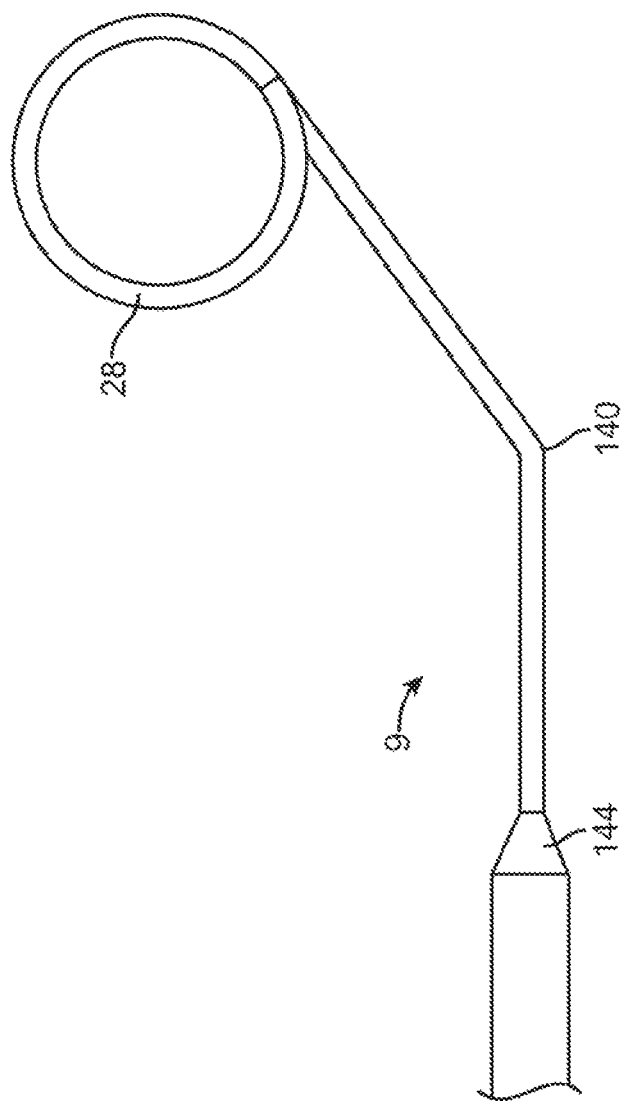
FIG. 12 illustrates an embodiment of a steerable guidewire for use with the intravenous catheter and insertion device.

FIG. 12 illustrates another embodiment of a guidewire 9 for use with the intravenous catheter 100 and insertion device 20 of the present invention. The guidewire 9 may be made from a uniform-diameter wire or a tapered wire and may optional be supported by a support tube 8 as described above. The spiral distal curve 28 of the guidewire 9 may be any of the configurations described or incorporated herein. There is a bend 140 of approximately 30 to 60 degrees in the guidewire 9 a short distance, for example 1 to 5 mm, proximal to the spiral distal curve 28. The bend 140 may be located just at the distal end 144 of the support tube 8 or, optionally, the bend 140 may be located a short distance, for example 1 to 5 mm, distal to the distal end 144 of the support tube 8. The bend 140 allows the guidewire 9 to be used in a steerable fashion to facilitate negotiating tortuous and/or branching blood vessels.

While the present invention has been described herein with respect to the exemplary embodiments and the best mode for practicing the invention, it will be apparent to one of ordinary skill in the art that many modifications, improvements and subcombinations of the various features and embodiments, adaptations and variations can be made to the invention without departing from the spirit and scope thereof.

What is claimed is:

1. A method for inserting a catheter into a patient, comprising:
   providing a catheter insertion device including:
      a housing;
      a needle attached to a needle carrier, the needle and the needle carrier designed to move relative to the housing;

a catheter including a catheter shaft attached to a catheter hub, the catheter shaft positioned coaxially over the needle, the catheter hub including a closed proximal chamber separated from a distal chamber by a septum; and a guidewire having a coil tip including a straightened configuration and a coiled configuration, the coil tip positioned in a lumen of the needle in the straightened configuration, the guidewire designed to move relative to the housing and the needle;

inserting a distal end of the needle and the catheter shaft into a blood vessel of the patient;

advancing the coil tip out of the needle lumen, wherein the coil tip transitions from the straightened configuration to the coiled configuration in the blood vessel;

advancing the catheter shaft over the guidewire; and withdrawing the guidewire and the needle from the catheter, wherein the coil tip transitions from the coiled configuration to the straightened configuration in the catheter shaft, and from the straightened configuration to the coiled configuration in the closed proximal chamber of the catheter hub.

2. The method according to claim 1, wherein the withdrawing step comprises releasing a biasing member coupled to the needle carrier to urge the needle carrier toward a proximal end of the housing.

3. The method according to claim 2, wherein a proximal end of the guidewire is simultaneously urged toward the proximal end of the housing along with the needle carrier.

4. The method according to claim 2, wherein a proximal end of the guidewire is urged toward the proximal end of the housing after the needle carrier.

5. The method according to claim 4, wherein the needle carrier and the proximal end of the guidewire are urged toward the proximal end of the housing via a single activation of an actuating member.

6. The method according to claim 4, wherein the needle carrier and the proximal end of the guidewire are urged toward the proximal end of the housing via two separate activations of an actuating member.

7. The method according to claim 1, wherein the withdrawing step comprises manually moving the needle carrier and a proximal end of the guidewire toward a proximal end of the housing.

8. The method according to claim 7, wherein the withdrawing step comprises simultaneously moving the needle carrier and the proximal end of the guidewire toward the proximal end of the housing.

9. The method according to claim 1, wherein the catheter hub includes a septum and a wiping element positioned proximal to the septum, further comprising moving the coil tip through the septum and the wiping element.

10. The method according to claim 1, further comprising moving an actuator handle distally to advance the guidewire in a distal direction and moving the actuator handle laterally to initiate the withdrawing step.

11. The method according to claim 1, wherein the catheter hub includes a wiping element proximal to the septum, wherein the withdrawing step comprises moving the coil tip from the distal chamber to the closed proximal chamber through the septum, and from the closed proximal chamber out of the catheter hub through the wiping element.

12. The method according to claim 11, wherein following the step of moving the coil tip through the wiping element, the coil tip is distal to a distal end of the housing and visible to a user.

13. The method according to claim 1, wherein the catheter insertion device further comprises an interlocking member in the housing engaged with a mating interlocking member on the needle carrier, wherein a compression spring is initially in a compressed state and constrained by engagement of the interlocking member with the mating interlocking member, and wherein an actuator mechanism is actuated to disengage the mating interlocking member from the interlocking member, thus releasing the compression spring to urge the needle carrier in a proximal direction.

* * * * *